US006326007B1

(12) United States Patent
Yilma et al.

(10) Patent No.: US 6,326,007 B1
(45) **Date of Patent: *Dec. 4, 2001**

(54) ATTENUATED LENTIVIRUS VECTORS EXPRESSING INTERFERON

(75) Inventors: Tilahun D. Yilma; Luis D. Giavedoni; Paul A. Luciw, all of Davis, CA (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/504,723

(22) Filed: Jul. 20, 1995

(51) Int. Cl.[7] .......................... A61K 39/21; C07H 21/00; C07K 14/155; C12N 7/04

(52) U.S. Cl. .................................... 424/207.1; 424/187.1; 424/199.1; 424/205.1; 424/208.1; 435/235.1; 435/236; 435/320.1; 514/44; 530/350; 536/23.1; 536/23.72

(58) Field of Search ............................. 435/320.1, 235.1, 435/236; 424/205.1, 207.1, 187.1, 199.1, 208.1; 514/44; 530/350; 536/23.1, 23.72

(56) References Cited

U.S. PATENT DOCUMENTS 5,739,118 * 4/1998 Carrano et sl. .

OTHER PUBLICATIONS

Haynes et al. Ann. Med., 1996, vol. 28, p. 39–41 Trends in Molecular Medicine, "Update on the Issues of HIV vaccine Development", 1996.*

Luciw et al. "Replication–competent Simian immunodeficiency Virus (SIV) Vectors for Expression of Cytokine Genes. . . " J Med Primatology 24(4), 1995, p. 183.*

Dougan et al. "Live Oral Salmonella Vaccines: potential use of Attenuated Strains as Carriers of Heterologous Antigens . . . " Parasite Immunol 1987, 9, p. 151–160.*

Schodel et al. "Recognition of a Hepatitis B Virus Nucleocapsid T–cell Epitope expressed as a Fusion Protein . . . " Vaccine 8 (5), Oct. 1990, p569–572.*

Harrison et al. "Inhibition of Human Immunodeficiency Virus–1 Production Resulting from Transduction . . . " Human Gene Therapy 3:461–469, 1992.*

Durum et al. "Proinflammatory Cytokines and Immunity" *Fundamental Immunology*, 3rd ed. 1993. p 801–835.*

Fox "No Winner aganist AIDS" Bio/Technology vol. 12 Feb. 1994, p 128.*

Daniel, M.D., et al., "Protective Effects of a Live Attenuated SIV Vaccine with Deletion in nef Gene", *Science*, 258:1938 (1992).

Fischl, M.A., "Antiretroviral Therapy in Combination with Interferon for AIDS–Related Kaposi's Sarcoma", *Am. J. Med.*, 90:2S (1991).

Flexner, C., et al., "Prevention of vaccinia virus infection in immunodeficient mice by vector–directed IL–2 expression", *Nature* (London), 330:259 (1987).

Giavedoni, L. D., et al., "Vaccinia virus recombinants expressing chimeric proteins of human immunodeficiency virus and γ interferon are attenuated for nude mice", *Proc. Natl. Acad. Sci. USA*, 89:3409 (1992).

Gibbs, James S., et al., "Construction and In Vitro Properties of HIV–1 Mutants with Deletions in 'Nonessential' Genes", *AIDS Res. and Human Retroviruses*, 10:343 (1994).

Gibbs, James S., et al., "Construction and In Vitro Properties of $SIV_{mac}$ Mutants with Deletions in 'Nonessential' Genes", *AIDS Res. and Human Retroviruses*, 10:607 (1994).

Girard, M., et al.,"Immunization of chimpanzees confers protection against challenge with human immunodeficiency virus", *Proc. Natl. Acad. Sci. USA*, 88:542 (1991).

Jamieson, B. D., et al., "Requirement of Human Immunodeficiency Virus Type 1 *nef* for In Vivo Replication and Pathogenicity", J. Virology, 68:3478 (1994).

Kestler, H. W., et al., "Importance of the nef Gene for Maintenance of High Virus Loads and for Development of AIDS", *Cell*, 65:651 (1991).

Kohonon–Corish, M. R. J., et al., "Immunodeficient mice recover from infection with vaccinia virus expressing interferon–γ", *Eur. J. Immunol.*, 20:157 (1990).

Luciw, P. A., et al., "Genetic and Biological Comparisons of Pathogenic and Nonpathogenic Molecular Clones of Simian Immunodeficiency Virus ($SIV_{man}$)", *AIDS Res. Hum. Retroviruses*, 8:395 (1992).

Maniatis, *Molecular Cloning: A Laboratory Manual*, (Cold Spring Harbor) Laboratory Press, 2d ed., 1989.

Marthas, M. L., et al., "Efficacy of live–attenuated and whole–inactivated simian immunodeficiency virus vaccines against vaginal challenge with virulent SIV", *J. Med. Primat.*, 21:99 (1992).

Murphy, B. R., et al., Immunization against viruses, Chapter 15, *In:Fundamental Virology*, Fields, B. N., Knipe, D. M., et al. (eds.), New York, Raven Press, Ltd. (1991).

(List continued on next page.)

*Primary Examiner*—Phuong T. Bui
(74) *Attorney, Agent, or Firm*—Townsend and Townsend and Crew LLP

(57) ABSTRACT

This invention discloses recombinant vectors and live attenuated pathogens produced by these vectors which are useful as vaccines and therapeutic agents. Particularly disclosed are live attenuated recombinant viruses that remain at very low virus loads, and preferably do not persist in the infected hosts. These recombinant viruses are useful against retroviruses such as human immunodeficiency virus and against acquired immunodeficiency diseases. In the recombinant vectors and pathogens, one or more genes, or part of the gene(s), responsible for pathogenesis have been completely or partially rendered nonfunctional, e.g., by full or partial deletion or mutagenesis. Further, the recombinant vectors and pathogens contain one or more genes encoding cytokine(s) and/or lymphokine(s).

21 Claims, 5 Drawing Sheets

OTHER PUBLICATIONS

Ramshaw, I. A., et al., "Recovery of immunodeficient mice from a vaccinia virus IL–2 recombinant infection", *Nature*, 329:545 (1987).

Regier, D. A., et al., The Complete Nucleotide Sequence of a Molecular Clone of Simian Immunodeficiency Virus, *AIDS Res. Hum. Retroviruses*, 6:1221 (1990).

Riggin, C. H., et al., "Effect of Interferon on the Exogenous Friend Murine Leukemia Virus Infection", *Virology*, 118:202 (1982).

Salk, J., et al., "A Stratagy for Prophylactic Vaccination Against HIV", *Science*, 260:1270 (1993).

Shibata, R., et al., "Generation of a Chimeric Human and Simian Immunodeficiency Virus Infectious to Monkey Peripheral Blood Mononuclear Cells", *J. Virol.*, 65 (7):3514 (1991).

Yang, N., et al., *Gene Therapeutics*, J. A. Wolff, ed., Birkhauser, MA USA (1994).

Yilma, T., et al., "Enchancement of Primary and Secondary Immune Responses by Interferon–Gamma", *Adv. Exp. Med. Bio.*, 251:145 (1989).

Poster 78 from "Conference on Advances in AIDS Vaccine Development: 1994, 7th Ann. Mtg. of the Nat'l Cooperative Vaccine Development Groups for AIDS", Div. of AIDS, Nat'l. Inst. of Allergy and Infectious Diseases, Reston, VA (1994).

Abstract P25–9 from "Scientific Programs and Abstracts", American Society for Virology, 13th Ann. Mtg., Madison, WI (1994).

* cited by examiner

```
SEQUENCE LISTING


(1) GENERAL INFORMATION:

   (iii) NUMBER OF SEQUENCES:  10


(2) INFORMATION FOR SEQ ID NO:1:

     (i) SEQUENCE CHARACTERISTICS:
          (A) LENGTH:  20 base pairs
          (B) TYPE:  nucleic acid
          (C) STRANDEDNESS:  single
```

-continued (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:1:

GTACCATGGC CAAATGCAAG 20

(2) INFORMATION FOR SEQ ID NO:2:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:2:

ATAGACATGT CGACTTTTAT 20

(2) INFORMATION FOR SEQ ID NO:3:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: YES (xi) SEQUENCE DESCRIPTION: SEQ ID NO:3:

ATTGTCGACC CTCACAAGAG 20

(2) INFORMATION FOR SEQ ID NO:4:

(i) SEQUENCE CHARACTERISTICS:
(A) LENGTH: 20 amino acids
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: YES (xi) SEQUENCE DESCRIPTION: SEQ ID NO:4:

TGCTAGGAAT TCTCCTGCTT 20

(2) INFORMATION FOR SEQ ID NO:5:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: DNA (genomic)

-continued (iii) HYPOTHETICAL: YES (iv) ANTI-SENSE: NO (xi) SEQUENCE DESCRIPTION: SEQ ID NO:5:

CTGACCTACC TACAATACGG GTGGAGCTAT TTCCACGAGG CGGTCCAGGC C 51

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: YES (xi) SEQUENCE DESCRIPTION: SEQ ID NO:6:

AAATCCCTTC CAGTCCCCCC 20

(2) INFORMATION FOR SEQ ID NO:7:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:7:

GCTATAAGTT GGGCGGCCGC TGGTCAAAAA CG 32

(2) INFORMATION FOR SEQ ID NO:8:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: YES (xi) SEQUENCE DESCRIPTION: SEQ ID NO:8:

CTCTCCTTTA GCGGCCGCTT CTATCT 26

(2) INFORMATION FOR SEQ ID NO:9:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES

-continued

```
    (iv) ANTI-SENSE:  NO

    (xi) SEQUENCE DESCRIPTION: SEQ ID NO:9:

GCTTCTAGAT AATACAGTAG CAACCCTCTA TTG                              33


(2) INFORMATION FOR SEQ ID NO:10:

     (i) SEQUENCE CHARACTERISTICS:
          (A) LENGTH:  37 base pairs
          (B) TYPE:  nucleic acid
          (C) STRANDEDNESS:  single
          (D) TOPOLOGY:  linear

    (ii) MOLECULE TYPE:  DNA (genomic)

   (iii) HYPOTHETICAL:  YES

    (iv) ANTI-SENSE:  YES

    (xi) SEQUENCE DESCRIPTION: SEQ ID NO:10:

GTCGGCCTTA AAGGCCCTGG GGCTTGTTCC ATCTATC                          37
```

ATTENUATED LENTIVIRUS VECTORS EXPRESSING INTERFERON

This invention was partially made with Government support under Grant Nos. AI-29207, RR-00169, and AI-27732 awarded by the National Institute of Health. The Government has certain rights to this invention.

FIELD OF THE INVENTION

This invention relates to the field of vaccines, particularly live attenuated recombinant pathogens that remain at very low microbial loads, and preferably do not persist in the vaccinated hosts. The preferred vaccines are recombinant viruses that are especially useful against retroviruses such as human immunodeficiency virus and against acquired immunodeficiency diseases.

BACKGROUND OF THE INVENTION

Human immunodeficiency virus (HIV) and simian immunodeficiency virus (SIV)

Despite voluminous research from many different fronts, the development of safe, effective vaccines against the human immunodeficiency virus (HIV) has proven to be difficult. Like other lentiviruses, HIV has a remarkable ability to persist and to eventually induce a chronic, debilitating disease despite an apparently strong host immune response to the virus. HIV-infected humane may remain clinically well for years while maintaining detectable humoral and cellular immune responses, only to succumb eventually to the virus.

Simian immunodeficiency virus (SIV) is a nonhuman primate lentivirus that is the closest known relative of HITV-1 and HIV-2 strains. SIV closely parallels its human counterparts in genetic organization and biological properties. Similarities between SIV and HIV include: lentiviral morphology; tropism for CD4 lymphocytes and macrophages; extra genes called tat, rev, vif, vpr, and nef that other retroviruses are not known to have; use of the CD4 molecule for receptor; cytopathicity; and the ability to cause chronic disease after long-term persistent infection. All replication-competent retrovirus genomes contain gag (group-specific core antigen), pol (polymerase), and env (envelope) genes. HIV-1 has at least six additional genes: viral infectivity factor (vif), vpr, vpu, transactivator (tat), regulator of viral expression (rev) and negative effector (nef) genes; SIV from rhesus macaques (*Macaca mulatta*) and HIV-2 have a similar set of accessory genes as HIV-1 except that instead of vpu, the latter two have vpx. The vif, vpr, vpu, vpx, and nef genes have been termed "nonessential" since they can be deleted without completely abrogating the ability of the virus to replicate (Kestler, H. W., et al., *Cell*, 65:651–662 (1991)). Unique strains of SIV have been recovered from several African primate species. In the natural host of origin, these viruses establish a latent or persistent infection and appear not to cause disease. Distinct strains of SIV have also been recovered from captive Asian macaques. An SIV from rhesus macaques ($SIV_{mac}$) and one from a sooty-mangabey monkey ($SIV_{smm}$) cause persistent infections in experimentally inoculated macaques, resulting in acquired immunodeficiency diseases (AIDS)-like disease that is similar to AIDS in individuals infected with HIV-1 or HIV-2, which involves immunodeficiency and opportunistic infections, and results in death {McCune, J. M., *Cell*, 64:351–360 (1991) and Simon, M. A., et al., *AIDS Res. Hum. Retroviruses*, 8:327–337 (1992)}. SIV uses the same CD4 receptor as does HIV on human T cells, and it can be blocked with the same monoclonal antibodies. Molecular clones of SIV isolates from several primate species show a genomic organization that is similar to that of HIV, and phylogenetic analysis of viral genome sequences has revealed the close evolutionary relationships of these simian and human lentiviruses {Myers, G., et al., Los Alamos National Laboratory, Los Alamos, N. Mex. (1992)}. Based on the antigenic genetic morphologic and functional similarities shared by HIV and SIV, SIV infection of macaques has come to be recognized as an animal model for HIV infection and AIDS {Hirsch, V. M., et al., *Virology*, 3:175–183 (1992)}. This animal model is critical for elucidating mechanisms of pathogenesis and for the development of vaccines and anti-viral therapies. The above factors, together with the close immunological relationship of primate genera, argue that a vaccine proven to be effective in protecting rhesus macaques from infection and disease after experimental challenge with SIV will likely be effective in protecting humans at risk for HIV infection and AIDS {Murphey-Corb, M., et al., *Science*, 246:1293–1297 (1989)}.

Two closely related molecular clones of $SIV_{mac}$ ($SIV_{mac239}$ and $SIV_{mac1A11}$) have been extensively characterized iil vitro and in vivo. At the New England Regional Primate Research Center, a provirus was molecularly cloned from the $SIV_{mac239}$ isolate to produce a cloned virus that was also designated $SIV_{mac239}$ {Naidu, Y. M., et al., *J. Virol*, 92: 491–4696 (1988)}. This clone replicates in peripheral blood mononuclear cells (PBMCS) but is restricted in macrophages {Bancroft, A. J., et al., *J. Immunol.*, 150:1395–402 (1993) and Ringler, D. J., et al., *Lab. Inves.*, 62:435–43 (1990)}. $SIV_{mac1A11}$, cloned at the Department of Medical Pathology, University of California, Davis, infects rhesus macaque PBMCs and both monocyto-derived and alveolar macrophages {Marthas, M. L., et al., *J. Med. Primat.*, 18:311–319 (1989); Bancroft, A. J., et al., *J. Immunol.*, 150:1395–402 (1993) and Unger, R. E., et al., *J. Med. Primatol.*, 24:74–81 (1992)}. The complete sequences of the proviral clones of $SIV_{mac1A11}$ (GenBank accession number M76764) and $SIV_{mac239}$ (GenBank accession number 33262) have been determined, the genes for these viruses show greater than 95% homology {Luciw, P. A., et al., *AIDS Res. Hum. Retroviruses*, 8:395–402 (1992) and Regier, D. A., et al., *AIDS Res. Hum. Retroviruses*, 6:1221–1231 (1990)}.

Previous attempts to develop vaccines for SIV have either failed to provide immunity or had limited success. Inactivated whole-virus, virion subunits, and live recombinant subunit vaccines have all provided limited or no protective immunity against infection with virulent STV in rhesus macaques. Inactivated whole-virus vaccines have provided protective immunity to macaques against challenge with SIV propagated in human, but not rhesus, PBMCs {Carlson, J. R., et al., *Aids Research and Human Retroviruses*, 6:1239–1246 (1990); Desrosiers, R. C., et al., *Proc. Natl. Acad. Sci. USA*, 86:6353–6357 (1989); Johnson, P. R., et al., *Proc. NatlAcad. Sci. USA*, 99:2175–2179 (1992); Murphey-Corb, M., et al., *Science*, 246:1293–1297 (1989) and Gardner, M. B.; *AIDS/HIV Treatment Directory*, compiled and published by AmFAR, Vol. 6: 5–10 (1992)}. Evidence has been presented that the protective antigens were not viral but human cellular antigens (HLA DR, β2m, and HLA class I) {Arthur, L. O., et al., *Science*, 258:1935–1938 (1992); Langlois, A. J., et al., *Science*, 255:292–293 (1992); Stott, E. J., *Nature*, 253;393 (1991) and Sutjipto, S., et al., *J. Virol*, 64:2290–7 (1990)}.

a) $SIV_{mac1A11}$: In rhesus macaques infected by the intravenous route (IV), $SIV_{mac1A11}$ establishes a low virus load in which virus can be isolated from PBMCs during the first 2 to 6 weeks post-infection, but is not recoverable from PBMCs for observation periods of up to three years thereafter (Marthas, M. L., et al., *J. Med. Primal.*, 18:311–319 (1989) and Marthas, M. L., et al., *J. Virol.*, 64:3694–3700 (1990)). Macaques infected with $SIV_{mac1A11}$ have remained healthy over three years {Marthas, M. L., et al., *J. Virol.*, 64:3694–3700 (1990); Marthas, M. L., et al., *J. Virol.*, 67:6047–6055 (1993)). Because $SIV_{mac1A11}$ in macaques (I) caused no signs of disease, (ii) established a low virus load, and (iii) induced antiviral immune responses, its efficacy as a live attenuated vaccine was tested {Marthas, M. L., et al., *J. Virol.*, 64:3694–3700 (1990)}. Macaques immunized with $SIV_{mac1A11}$ were resistant to infection with a low dose of uncloned pathogenic $SIV_{mac251}$, a strain distinct from but closely related to $SIV_{mac239}$, inoculated by the IV route {Marthas, M. L., et al., *J. Virol.*, 67:6047–6055 (1993)}. However, macaques immunized with the live attenuated virus were not protected from challenge with virulent virus by the intravaginal route {Marthas, M. L., et al., *J. Virol.*, 67:6047–6055 (1993)}.

b) $SIV_{mac239}$ and $SIV_{mac239\Delta nef}$: In rhesus macaques infected by the IV route, $SIV_{mac239}$ persists at relatively high virus loads and causes a fatal AIDS-like disease, generally in a period ranging from 6 months to one and one-half years after injection {Kestler, H. W., et al., *Science*, 248:1109–1112 (1990)}. The nef gene of $SIV_{mac239}$ is prematurely truncated by a stop codon {Regier, D. A., et al., *AIDS Res. Hum. Retroviruses*, 6:1221–1231 (1990)}. The nef gene is encoded by an open reading frame located at the 3' end of the HIV and SIV genomes that extends from the end of env and partially overlaps the 3' LTR. Net encodes an early, non-structural, intracellular protein whose biochemical function and in vitro effect on virus growth are still in dispute {Kestler, H. W., et al., *Cell*, 65:651–662 (1991)}.

Analysis of $SIV_{mac239}$ recovered from infected animals revealed that a reversion in the stop codon, which truncates the nef gene, occurred in vivo to produce viral genomes encoding full-length nef genes ($SIV_{mac239/nef-open}$) {Kestler, H. W., et al., *Cell*, 65:651–662 (1991)}. Thus, it was inferred that the nef gene is important for viral pathogenesis. Accordingly, a clone with a large non-reversible deletion of nef was constructed to produce the virus designated $SIV_{mac239\Delta nef}$. Tests of the nef-deleted virus in rhesus macaques revealed that virus loads were low (compared to macaques infected with $SIV_{mac239}$), antiviral antibodies were induced, and infected animals remained healthy for more than 3 years after infection {Daniel, M. D., et al., *Science*, 258:1938–1941 (1992)}.

The vaccine potential of the live-attenuated $SIV_{mac239\Delta nef}$ was tested by immunizing macaques with this virus and then challenging with virulent virus strains (i.e., cloned $SIV_{mac239/nef-open}$ and uncloned $SIV_{mac251}$) {Daniel, M. D., et al., *Science*, 258:1938–1941 (1992)}. Evaluation of plasma antigenemia and virus loads in PBMCs revealed that three of four immunized animals showed no signs of infection after challenge with $SIV_{mac239/nef-open}$. One of these four immunized animals demonstrated a transient infection: virus was recovered from PBMCs at four weeks after challenge. In addition, two of these macaques were protected from challenge with 1000 animal infectious doses (AID) of uncloned $SIV_{mac251}$. However, $SIV_{mac239\Delta nef}$ causes persistent infection in macaques, a major limitation for its use as a vaccine {Daniel, M. D., et al., *Science*, 258:1938–1941 (1992)}.

Immunoregulatory effects of interferon-gamma (IFN-γ)

IFN-γ is a pleiotropic lymphokine with potent immunoregulatory, antineoplastic, and antiviral properties.

IFN-γ can be produced either by $CD4^+$ T cells in response to antigen presented in the context of major histocompatibility complex (MHC) class II molecules, or by $CD8^+$ cytotoxic T lymphocytes following recognition of antigen associated with MHC class I. In addition, NK cells secrete IFN-γ after exposure to tumor necrosis factor-α and microbial products. IFN-γ is also produced by gamma-delta T cells. This event represents the host's first line of defense against microbial pathogens susceptible to killing by activated macrophages Farrar, M. A., et al., *Ann. Rev. Immunol*, 11:571–611 (1993)}. In animal models, IFN-γ modulates macrophage tumoricidal and microbicidal activity {Pace, J. L., et al., *J. Immunology*, 130:2011 (1983) and Salk, J., et al., *Science*, 260:1270–1272 (1993)}, NK cell cytolysis {Welsh, R., *Curr. Topics Microbial Immunol.*, 92:83–106 (1981)}, and both B and T cell responses to antigens {Frasca, D., et al., *J. Immunol.*, 134:3907–3011 (1985) and Nakamura, M., *Nature* (London), 307:361–362 (1984)}. This lymphokine also upregulates expression of class I MHC molecules on target cells {Bukowski, J. F., et al., *J. Exp. Med.*, 161;257–262 (1985)}.

The IFN-γ in vitro antiviral activity has been demonstrated against a number of viruses including encephalomyocarditis virus (EMCV), herpes simplex virus (HSV), rhinovirus, vaccinia virus and HIV {Naidu, Y. M., et al., *J. Virol.*, 62: 4691–4696 (1988); Nakamura, M., 307:361–362 (1984); Naso, R. B., et al., *J. Int. Res.*, 2:75–96 (1982) Odean, M. J. et al. , *Infection & Immunity*, 58:427–32 (1990); Pace, J. L., et al., *J. Immunology*, 130:2011 (1983); Playfair, J. H. L., et al., *Clin. Exp. Immunol*, 67:5–11 (1987)}. Clinical trials of interferon-α in AIDS patients are being conducted based on the inhibitory effects of interferon in tissue culture {see e.g. Fiscal, M. A., *Am. J. Med.*, 90:2 (1991)}.

Vaccinia virus (V.V.) recombinants that express cloned genes encoding antigens of unrelated infectious agents, such as hepatitis B virus and HIV, have been used to develop live vaccines that are not as dangerous as using recombinant hepatitis B virus and HIV. However, though V.V. recombinants have reduced pathogenicity, severe complications could occur after vaccination, especially in immunodeficient individuals {see discussion in Ramshaw, I. A., et al., *Nature*, 329;545–546 (1987)}. Thus, attempts have been made to modify these recombinant VV and it has been shown that coexpression of interleukin 2 (IL-2) and murine (MuIFN-γ) in VV completely abolishes the lethal effects of the virus in nude mice {Ramshaw, I. A., et al., *Nature*, 329:545–546 (1987); Flexner, C., et al., *Nature*, 330:259–262 (1987); Kohonen-Corish, M. R. J., et al., *Eur. J. Immunol.*, 20:157–161 (1990)}.

VV recombinants expressing fusion proteins of human or murine IFN-γ and HIV structural proteins were attenuated for athymic nude mice and are completely cleared in 7 days after exposure to high doses of this virus. Inoculation of nude mice with 100 pfu of VV results in 100% mortality in 10 days, whereas $10^7$ pfu of VV expressing IFN-γ do not cause disease {Giavedoni, L. D., et al., *Proc. Natl. Acad. Sci. USA*, 89:3409–3413 (1992)}.

SUMMARY OF THE INVENTION

Is one aspect of the present invention presents non-naturally occurring, live attenuated microbial pathogens (hereinafter referred to as "pathogens") which remain at very low microbial loads compared to unattenuated pathogens, in an infected host. For example, in the case of the live attenuated viruses of the present invention, the virus load is preferably between 10 $TCID_{50}$ to 100 $TCID_{50}$, and is more preferably less than 10 $TCID_{50}$ per million cells in a host vaccinated with the virus. The term "$TCID_{50}$" denotes 50% tissue culture infectious doses. Most preferably, the live attenuated pathogens do not persist in the infected host. Further, the attenuated pathogens are attenuated in pathogenicity and not lethal to the host, but are capable of eliciting and enhancing the host's immune response against the unattenuated pathogens from which the attenuated pathogens are derived. The attenuated pathogens are preferably replication-competent. These live attenuated pathogens are derived from naturally occurring members or related members of their pathogenic species. However, the attenuated pathogens are attenuated in their pathogenicity, for example, they do not contain one or more genes of the unattenuated pathogens which are responsible for pathogenicity, or these genes are partially or fully nonfunctional in the attenuated pathogens. More preferably,.these live attenuated pathogens are artificially derived from a pathogen, e.g. by recombinant method, by deleting or mutating the genes responsible for pathogenicity such that they are absent, rendered non-functional or partially functional. Further, these live attenuated pathogens are capable of producing one or more cytokines or lymphokines (hereinafter collectively referred to as "cytokines"), or one or more toxins, such as bacterial toxins which can enhance inflammatory processes, such as the S1 subunit of *B. pertussis*. These cytokines or toxins are preferably encoded by one or more exogenous genes which are introduced into the genomes of the attenuated pathogens by artificial means, such as by recombinant method. The preferred live attenuated pathogens are viruses, particularly live attenuated HIV, and the preferred cytokine is a human INF-γ. Said live attenuated pathogens are useful as vaccines or therapeutics against the pathogens from which they are derived and against their related pathogens and the diseases caused by them.

Another aspect of the invention presents recombinant vectors derived from pathogens but do not contain one or more genes of the pathogens which are responsible for pathogenicity, or these genes are partially or fully nonfunctional in the vectors. Further, these vectors are capable of expressing one or more cytokines. The vectors are useful for producing the above live attenuated pathogens.

Another aspect of the invention presents vaccination and therapeutic methods comprising administering to a host the above live attenuated pathogens or recombinant vectors.

Another aspect of the invention presents pharmaceutical compositions containing the above vectors or live attenuated pathogens useful as vaccines and therapeutics.

Another aspect of the invention presents methods for producing the above recombinant vectors and attenuated live pathogens.

BRIEF DESCRIPTION OF THE DRAWINGS

FIG. 3C graphically presents the data on the expression of IFN-γ by the SIV vector. The notations are as defined in FIG. 1, except that "Δnef" denotes SIV239Δnef.

In FIG. 4A, the molecular weight markers ("MWM") are: 2.0, 1.6, 1.0 and 0.5 kilobase pairs, respectively. In FIG. 4B, the MWM are: 3.0, 2.0, 1.6 and 1.0 kilobase pairs, respectively.

DETAILED DESCRIPTION OF THE INVENTION

Figure 1:
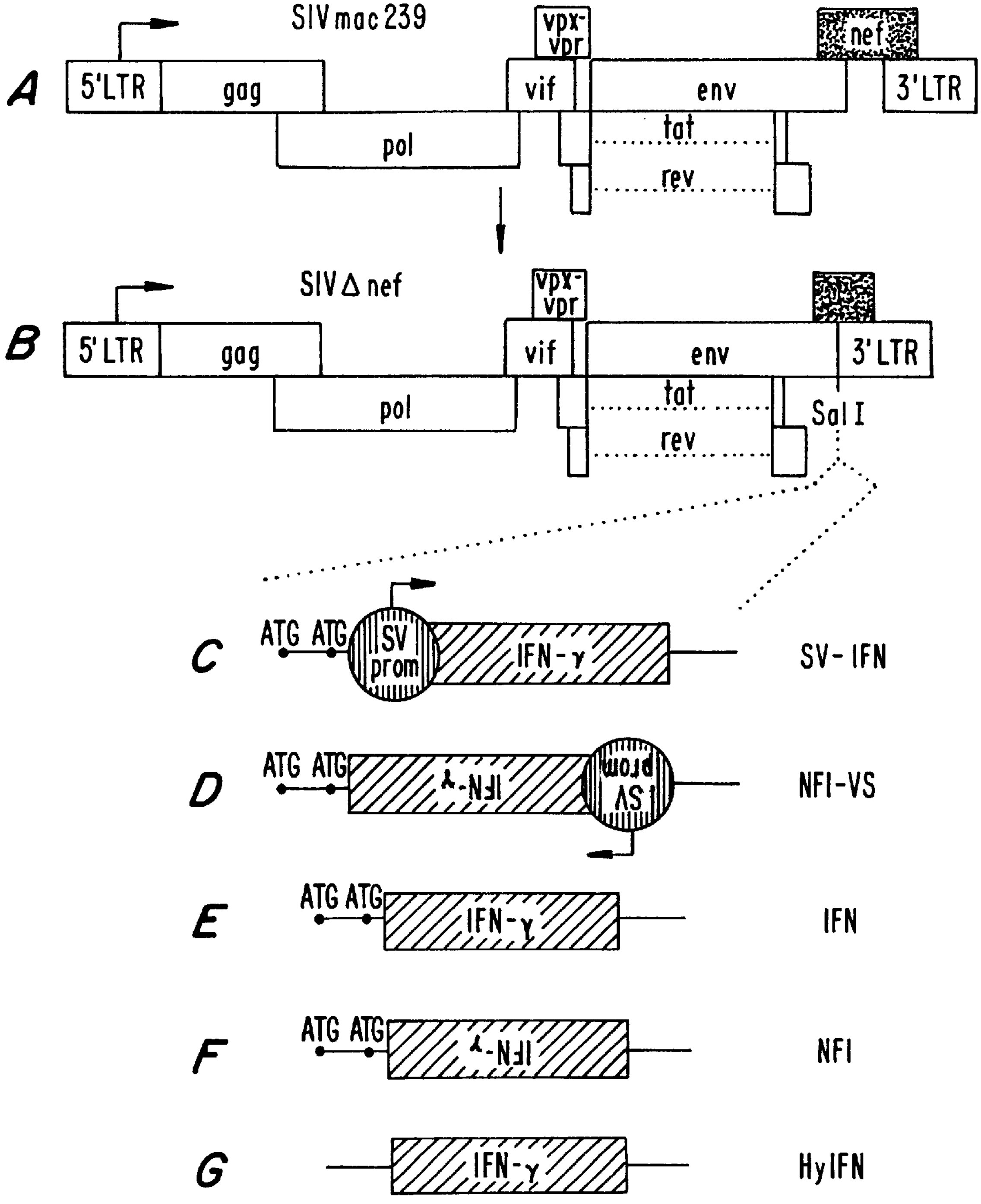
FIGS. 1A to 1G schematically present the strategy, starting from A. SIVmac239, for generating: B. SIV239Δnef (denoted SIVΔnef); C. SIVSV-IFN (denoted SV-IFN); D. SIVNFI-VS (denoted NFI-VS), E. SIVIFN (denoted IFN): F. SIVNFI (denoted NFI); and G. SIVHyIFN (denoted HyIFN).

The present invention presents live attenuated microbial pathogens (hereinafter referred to as "pathogens") which remain at very low microbial loads, and preferably do not persist in their vaccinated host. These pathogens are attenuated in pathogenicity and not lethal to the host. Preferably, the attenuated pathogens prevent initial infection of the host by the unattenuated pathogen, or limit dissemination and establishment of the unattenuated pathogen once it has infected the host. More preferably, the attenuated pathogens are capable of eliciting and enhancing the host's immune response against the unattenuated pathogens. Preferably, both the humoral and cellular immune responses are enhanced. The attenuated pathogens are preferably replication-competent. These live attenuated pathogens are related to or are naturally occurring members of their pathogenic species but they do not contain one or more genes of the pathogens which are responsible for their pathogenicity, or these genes are partially or fully nonfunctional in the attenuated pathogens. More preferably, the live attenuated pathogens are artificially derived from the unattenuated pathogens, e.g. by recombinant method, by deleting or mutating the genes responsible for pathogenicity such that they are absent, rendered non-functional or partially functional. More preferably, these live attenuated pathogens are additionally capable of expressing one or more cytokines or lymphokines (hereinafter collectively referred to as "cytokines") or toxins. Vectors for producing these live attenuated pathogens are also disclosed. Included in the definition of "vectors" are genomes of the attenuated pathogens, and their complementary nucleotide sequences, such as deoxyribonucleotide and ribonucleotide acid sequences (DNA and RNA, respectively). In the case of attenuated RNA viruses, the vectors may include the viral RNA genome, but proviral DNA and cDNA of the viral RNA are preferred. The present invention also presents methods for producing these live attenuated pathogens and recombinant vectors. The recombinant vectors are preferably produced by mutagenizing or deleting the genes responsible for pathogenicity from a pathogen, and inserting exogenous genes encoding the cytokines or toxins into the pathogen's genome. The live attenuated pathogens and recombinant vectors are useful vaccines and'therapeutics against the pathogens or related pathogens.

"Attenuation" as used herein is defined as reduced pathogenesis, with no disease or a significant delay or reduction in disease, e.g. reduced replication capacity of the pathogen is synonymous with attenuation. The live attenuated pathogens are more immunogenic and offer more durable and broader protection than other types of vaccines, because they best mimic infection with the (unattenuated) pathogens but do not retain the capacity to cause a full-blown disease. Therefore, they are more effective than vaccines based on inactivated whole pathogens, pathogenic subunits, or live pathogens based on heterologous pathogenic or bacterial vectors.

Lymphokines and cytokines are herein collectively referred to as "cytokines" and are proteins or peptides having iminunomodulating effects on humoral and cellular responses in an animal. Cytokines generally are capable of one or more of the following functions: inducing antiviral state in uninfected cells; activating mononuclear phagocytism; enhancing immune memory response to a pathogen; modulating macrophage tumoricidal and microbicidal activity, NK cell cytolysis, and both B and T cell responses to antigens; and upregulating expression of class I MHC molecules on target cells. The cytokines preferably enhance the immune response of the vaccinated hosts which eventually kill any live attenuated pathogens remaining in the hosts.

Examples of the pathogens are! bacteria such as Mycoplasma, *Mycobacterium bovis*, and *Listeria monocytogenes*; viruses; and non-viral intracellular parasites such as organisms belonging to the genus Leishmania, Toxoplasma, and Plasmodium. The pathogens are preferably viruses, including both ribonucleic acid (RNA) and deoxyribonucleic acid (DNA) viruses. This invention is particularly useful for producing live attenuated viruses and recombinant vectors derived from viruses which persist in their infected host. The preferred target viruses are retroviruses, and more preferably, lentiviruses. Examples of lentiviruses are: SIV, HIV, feline immunodeficiency virus (FIV), bovine immunodeficiency virus (BIV), equine infectious anemia virus (EIAV), caprine arthritis encephalitis virus (CAEV). The most preferred retroviruses to derive the live attenuated viruses and recombinant vectors are: SIV and HIV.

An example of a gene that is responsible for pathogenesis, but which is absent, or fully or partially nonfunctional in the attenuated live pathogens and recombinant vectors is a regulatory or accessory gene. Preferably, these are nonessential genes, i.e. genes which can be deleted without completely abrogating the ability of the pathogen to replicate. In lentiviruses, examples of the genes are: nef, vif, tat, vpr, vpu, and vpx genes. More preferably, the genes are not required for productive infection but influence latency and reactivation, e.g., deletion of thymidine kinase (tk) gene and missense mutation in the tk gene reduces the neurovirulence and causes a decrease or loss of the ability of HSV-1, and HSV-2 to reactivate in mice {See Murphy, B. R., & Chanock, R. M., *Fundamental Virology*, 2d Ed., Fields B. N., et al., ed., Ch. 15, at p. 394, Raven Press Ltd., NY (1991)}.

Examples of the cytokine genes are genes that encode: IFN-α, IFN-β, IFN-γ, interleukin-2 (IL-2), and interleukin-12 (IL-12). The preferred cytokine is INF-γ. A cytokine which influences anti-viral mucosal immunity may be used. A cytokine regulating secretory antibody levels can be expressed by the vector, alone or in combination with other cytokine(s). The cytokine gene in a viral vector or live attenuated virus need not be under the control of a promoter, the long terminal repeats (LTR) are usually sufficient. An insertional mutagenesis; at the site of the pathogen gene can serve the dual goal of completely or partially deleting the pathogen gene, and inserting the cytokine gene. Besides the wildtype vectors or viruses, and those that are readily available or have been sequenced, the starting materials of the present invention may also be recombinant or attenuated vectors or viruses, preferably those with reduced pathogenicity. The selection of the starting material, the deletion or mutagenization of the regulatory or accessory genes, and the insertion of the cytokine genes into a vector, expression of the cytokine and the production of the live attenuated pathogens, can be achieved based on the present disclosure and using methods known in the art such as described in Maniatis, *Molecular Cloning: A Laboratory Manual*, (Cold Spring Harbor Laboratory Press, 2d ed., 1989), the references in the "Background of the Invention", and the "Example" section below. For example, insertion of genes can be accomplished by either in vitro ligation or in vivo homologous recombination. For example, in the case of viruses, either strategy may be carried out by manipulation of bacterial plasmids containing viral DNA sequences and the fragment to be cloned.

The vectors and live attenuated pathogens of the present invention can then be tested, for example, in the appropriate animal models or target animals using techniques known in the art for their vaccinating and therapeutic ability.

In particular, the present invention presents vaccines based on recombinant vectors and viruses, preferably recombinant lentiviral vectors and lentiviruses which contain one or more full or partial deletions in the nef, vif, tat, vpr, and vpx genes and express one or more cytokines. In the preferred embodiment, only the nef gene is deleted and the cytokine is IFN-γ. The most preferred recombinant vectors and viruses are derived from SIV and HIV useful for vaccination and treatment of SIV and HIV infections and diseases. In particular, the present invention discloses that persistent infection by $SIV_{mac239\Delta nef}$ can be eliminated by the expression of IFN-γ. In addition, the expression of IFN-γ not only attenuate $SIV_{mac239\Delta nef}$ but maintains the protective immune response of macaques to challenge with pathogenic uncloned $SIV_{mac251}$. The assessments of $SIV_{mac239\Delta nef}$ in vivo showed that it has a reduced virus load in vivo (i.e. there is a significant reduction in the release of infectious virus in vivo), does not cause disease, induces antiviral antibodies, and protects against challenge with virulent SIV. The most preferred recombinant vector and virus are $pSIV_{239\Delta nef}$ ATG/γ and SIVHyIFN, respectively, which are further described in the "Example" section below.

Since SIV is a known disease model for HIV, it is similarly contemplated that recombinant HIV vectors and viruses can be produced which contain one or more deletion in the nef, vif, tat, vpr, and vpf genes and which express one or more cytokines. In the preferred vectors and live attenuated viruses, the nef gene has been deleted and then replaced with, preferably human, IFN-γ gene. The recombinant HIV vectors and viruses are produced based on the method described in the "Example" section below, methods known in the art such as described in Maniatis, *Molecular Cloning. A Laboratory Manual* (Cold Spring Harbor Laboratory Press, 2d ed., 1989), and the references in the "Background of the Invention".

In the case of HIV, for example, the recombinant vectors and viruses can be derived from the HIV strain that has been used in most vaccine trials, the MN strain of HIV-1, whose principal neutralizing determinant (PND) is believed to be representative of approximately 60% of the isolates in North America. The recombinant vectors and viruses may also be derived from other HIV strains. The nucleic acid and amino acid sequences of all studied retroviruses, including HIV-1, HIV-2, and SIVs, are obtainable from a database, in both printed form and computer floppy disks, published annually by the Los Alamos National Laboratory, Los Alamos, N.

Mex., USA. The techniques for deleting one or more HIV regulatory genes and inserting the cytokine gene(s) can be similar to those described in the Examples below. Sequences for the cytokines known in the art can be used. For example, IFN-α, IFN-β, IL-2, IL-12 can be obtained from GCG GenBank, Madison, Wis., USA. Recombinant viruses and vectors which express the cytokine(s) at detectable level, preferably for more than 5 passages in culture, are selected and grown using methods known in the art, such as ELISA (enzyme-linked immunosorbent assay) for detecting the cytokines, or methods such as described in the Examples below.

The recombinant vectors and viruses can be first tested in chimpanzees which traditionally served as the animal model for HIV. The procedures for immunizing chimpanzees and testing the immunized chimpanzees for the efficacy of a vaccine to prevent or delay infection by HIV is as described in the literature, such as Girard, M., et al., *PNAS* (*USA*), 88:542–546 (1991) (herein incorporated by reference in its entirety) which also describes methods for challenging the immunized chimpanzees with virulent HIV viruses. In vivo stability of the recombinant virus and its viral loads or persistence in the chimpanzees may be determined based on the method described herein and in Example 5 below or methods known in the art. The chimpanzees will be immunized with the recombinant viruses and then challenged with the virulent viruses, i.e. if the recombinant viruses are derived from the MN strain of HIV-1, then the virulent MN viruses will be used as a challenge. If the immunized chimpanzees are protected, they will be challenged with more distant HIV-isolates. If broad protection is effective, the challenge with HIV-2 isolates will be performed. Preferably, in all cases, the immunized chimpanzees will be monitored for viremia, immunological and clinical parameters to determine whether the vaccine decreases virus load.

The following is an example of a regimen for challenge: (1) about 6 months post-immunization, immunized chimpanzees are challenged with a cell-free preparation of strain MN of HIV-1; (2) if these animals are protected against the homologous virus, then they will be test-challenged with more distant heterologous cell-free HIV-1-isolates and then HIV-2; (3) if protection is observed against heterologous virus, then vaccine efficacy will be tested against challenge with cell-associated virus. Cell-free virus will be used because virus titers can be accurately measured, and thus, different vaccine regimens can be rigorously compared within a study and between independent studies. The chimpanzees are preferably inoculated IV with challenge (virulent) viruses, because it is the most reproducible and reliable means of experimental infection. Immediately before inoculation with challenge virus, peripheral blood is collected by venipuncture in both heparinized and untreated vacutainers. After collecting these pre-challenge samples, chimpanzees will received 10 $AID_{50}$ of virulent cell-free virus in 1 ml of tissue culture medium (serum-free) by the IV route. Subsequent samples of peripheral blood and lymph node biopsies for various virological and immunological assessments will be collected and tested, for example, according to Table 1 below:

TABLE 1

| | Weeks post-infection | | | | | | | |
|---|---|---|---|---|---|---|---|---|
| Samples/Tests | 0* | 2** | 4* | 8* | 12* | 24** | 36* | 52 |
| Peripheral blood | | | | | | | | |
| anti-viral abs in plasma | + | + | + | + | + | + | + | + |
| plasma antigenemia | + | + | + | + | + | + | + | + |
| plasma viremia | + | + | + | + | + | + | + | + |
| CD4 cell number, CBC | + | + | + | + | + | + | + | |
| virus in PBMC | + | + | + | + | + | + | + | + |
| virus in CD4 cells | | + | | | | + | | + |
| virus in macrophages | | + | | | | + | | + |
| Lymph node biopsy | | + | | | | + | | + |
| Bone marrow biopsy | | + | | | | + | | + |

*10 ml of peripheral blood per chimpanzee
**20 ml of peripheral blood per chimpanzee Preferably, CBC (differential blood count and chemistry) and other clinical measurements-will be evaluated after challenge. $CD4^+$ T-cell values are used to assess effects of the recombinant virus infection on the chimpanzee lymphoid system {Girard, M., et al., *PNAS* (*USA*), 88:542–546 (1991) }. Peripheral blood is preferably collected by venipuncture, and differential cell counts performed to monitor hematological abnormalities. $CD4^+$ and $CD8^+$ T-cells are preferably enumerated in the pre-infection and post-infection by flow cytometry. Other clinical measurements such as eating patterns, diarrhea, and unusual behavior of the vaccinated chimpanzees will be noted daily. For example, body weight is measured once a week. Lymphadenopathy and splenomegaly are diagnosed by palpation, and any skin rash examined. Opportunistic infections (viral, bacterial, fungal) are diagnosed by standard microbiological techniques. Further, preferably plasma viremia, antigenemia, cell-associated virus load in PBMC, PCR for estimating viral DNA loads in infected chimpanzee cells molecular analysis of viral variants in vivo, and assessment of virus load in tissues, are performed using methods known in the art. Both humoral as well as CTL response to the recombinant viruses will be evaluated from immunized and control animals using methods known in the art, such as ELISA, VN (virus-neutralizing antibody), and Western Blot. Immune response analysis and virus isolation data are used to assess protection.

The vaccines are preferably chosen based on factors such as: low viral load in Vivo (Compared with animal infected with virulent virus), induction of antiviral antibodies or cellular response, and the fact that the infected animal remain healthy. Preferably, the vaccine is safe in very young recipients and immunocompromised individuals (e.g., individuals in developing countries who are malnourished and whose immune system may be weakened by other infectious agents), is capable of inducing broad immunity necessary to protect from diverse viral strains, protect challenge via cell-associated virus or across mucosal membranes.

The chosen vaccines are then tested in human using methods known in the art, such as methods which are similar to the tests applied to the chimpanzees above. The dosage to be administered is determined based on the tests on the animal model. For example, depending on the efficacy of the dosage in protecting the vaccinated chimpanzees against HIV challenge, it may be increased or diluted.

A similar strategy to the one explained for SIV and HIV, could be applied to other pathogens. For example, one or more pathogen genes involved in virulence can be eliminated, and one or more cytokine genes can be incorporated in such pathogen, thereby increasing its level of attenuation. The efficacy of the resulting attenuated pathogen can be determined in the appropriate animal model.

Some examples of genes that could become target for deletion or mutation (to render the genes nonfunctional or partially functional) are:

the sapG locus of the facultative intracellular bacterium *Salmonella typhimurium*, which encodes a product that is 99% identical to the $NAD^+$ binding protein TrkA, a component of a low-affinity $K^+$ uptake system in *Escherichia coli*. It has been shown that sapG mutants were killed by the antimicrobial peptide protamine in the presence of both high and low $K^+$, indicating that protamine hypersensitivity is not due to $K^+$ starvation {Parra-Lopez, C., et al., *Embo J.*, 13(17):3964–3972 (1994)}.

the neuraminidase/trans-sialidase and an acid-active, transmembrane pore-forming protein of the parasite *Typanosoma cruzi*, which are released by the parasite and are capable of acting together to accelerate rupture of the vacuolar membrane and the parasite's escape into the cytoplasm of the host cell. Escape from the parasitophorous vacuole allows virulent stages of *T. cruzi* to avoid compartmental, non-oxidative killing mechanisms such as degradation by lysosomal hydrolases {Hall, B. F., et al., *J. Eukaryotic Microbio.*, 40(2):207–213 (1993)}.

genes coding for proteins involved in the biosynthesis of the phosphoglycan moiety of the lipophosphoglycan (LPG) of *Leishmania major*, which is essential for intracellular survival of the parasite {McConville, M. J., et al., *J. Bio. Chem.*, 267(9):5855–5861 (1992)}.

genes whose products are not required for productive infection but influence latency and reactivation of a virus. An example of such a gene is the thymidine kinase (tk) gene of the herpes virus family and vaccina virus.

Vaccination and Therapeuetic Methods

The recombinant vectors of the present invention, such as plasmid proviral DNA, can be directly injected into a subject, to be vaccinated or treated, using methods known in the art, e.g. by microinjection or particle bombardment such as by gene gun (see e.g., Yang, N. et al., *Gene Therapeutics*, J. A. Wolff, ed., Birkhauser, Mass., USA (1994). Preferably, the recombinant vectors are solubilized in physiologically acceptable carriers. However, it is envisioned that intravenous injections and oral ingestion of the live attenuated viruses will be the primary route for vaccination or therapeutic administration of the vaccines of this invention, though intramuscular or subcutaneous administration may also be used. The recombinant viruses can be prepared for administration by mixing them at the desired degree of purity with physiologically acceptable carriers, i.e. carriers which are nontoxic to recipients at the dosages and concentrations employed, such as phosphate buffered saline solution.

The dosage of the recombinant vectors and viruses administered will depend upon the properties of the formulation employed, e.g., its binding activity and iil vivo plasma half-life, the concentration of the recombinant vectors and viruses in the formulation, the administration route, the site and rate of dosage, the clinical tolerance of the patient involved, the pathological condition afflicting the patient and the like, as is well within the skill of one skilled in the art. Different dosages may be utilized in a series of inoculations; the practitioner may administer an initial inoculation and then boost with relatively smaller doses of the recombinant vectors or viruses.

The recombinant vectors and viruses may also be used to vaccinate individuals who may or may not be at risk of exposure to HIV, and additionally, the vaccines are desirably administered to seropositive individuals and to individuals who have been previously exposed to HIV. The vaccine may also be administered to AIDS or ARC patients as therapeutics.

The other attenuated pathogens of this invention may also be used to vaccinate an animal or a human using methods similar to those described above, and if necessary, with modifications tailored to the particularities of the unattenuated pathogens and diseases involved, such as the infectious route. One skilled in the art would be able to determine the appropriate vaccination methods based on the teaching of the present invention and methods known in the art.

The examples in this application are presented to illustrate some aspects of the invention, and are not to be construed as limiting the scope of the invention.

EXAMPLES

Example 1

Recombinant: SIV Vector Constructions and Characterizations

This Example describes the construction and characterization of replication-competent SIV vectors expressing IFN-γ

MATERIALS AND METHODS

Cells and Viruses.

CEMx174 cells (available from the American Type Culture Collection, ATCC, Rockville, Md., USA) and rhesus PBMC were used for SIV isolation and propagation; these cells were maintained in RPMI (Roswell Park Memorial Institute Medium) supplemented with 10% fetal bovine serum. Human A549 cells (available from ATCC) were propagated in Dulbecco's modified Eagle's (DMEM) supplemented with 10% fetal bovine serum and antibiotics. $SIV_{mac239}$ and derivatives of the virus were propagated in either CEMx174 or rhesus PBMC. Encephalomyocarditis virus (EMCV) for the antiviral assay of human IFN-γ (HuIFN-γ) was propagated in A549 cells.

Construction of $SIV_{mac239\Delta nef}$.

The pathogenic molecular clone $SIV_{mac239}$ was used to construct SIV vectors {Kestler, H. W., et al., *Cell*, 65:651–662 (1991)}. First, a 186-base fragment of the nef coding sequence (between the end of env and the beginning of the 3'LTR) was deleted, and a unique SalI cloning site was incorporated at the position of the deletion for the insertion of the human IFN-γ gene (FIG. 1B). The cloning strategy involved PCR amplification of specific sequences with the following four oligonucleotide primers: Sense primers A ($^{5'}$GTACCATGGCCAAATGCAAG$^{3'}$, Nco I, nt. 8720) (SEQ ID NO:1) and C ($^{5'}$ATAGACATGTCGACTTTTAT$^{3'}$, Sal I, nt. 9681) (SEQ ID NO:2), and antisense primers B ($^{5'}$ATTGTCGAC CCTCACAAGAG$^{3'}$, Sal I, nt. 9401) (SEQ ID NO:3) and D ($^{5'}$TGCTAGGAATTCTCCTGCTT$^{3'}$, EcoRI, nt. 10530) (SEQ ID NO:4) [nucleotides numbers for $SIV_{mac239}$ are as in GenBank accession number M33262; restriction sites are underlined, and mutations appear in bold]. The plasmid pVP-2 (available from Dr. Paul A. Luciw, University of California, Davis, Calif., USA), containing the 3' half of $SIV_{mac239}$ provirus, was the template for all the PCR amplifications.

The region on the SIV genome encompassing the 3' half of env coding sequence was amplified with PCR primers A and B. Primer B incorporated two stop codons and a SalI site into the nef translation frame. The ends of the amplified DNA fragment were repaired with T4 DNA polymerase, and the DNA was cloned into the HindII site of the plasmid pBluescript (Promega Lab, Madison, Wis., USA) to generate pA+B. The plasmid with the new SalI site and the vector EcoRI site close to each other was selected. In a separate PCR reaction, primers e and D were used to generate a DNA fragment that included the 3'LTR of $SIV_{mac239}$ with SalI and EcoRI sites at the 5' and 3' ends, respectively. This fragment was digested with these two enzymes and cloned into plasmid pA+B to generate pAD.

Figure 2:
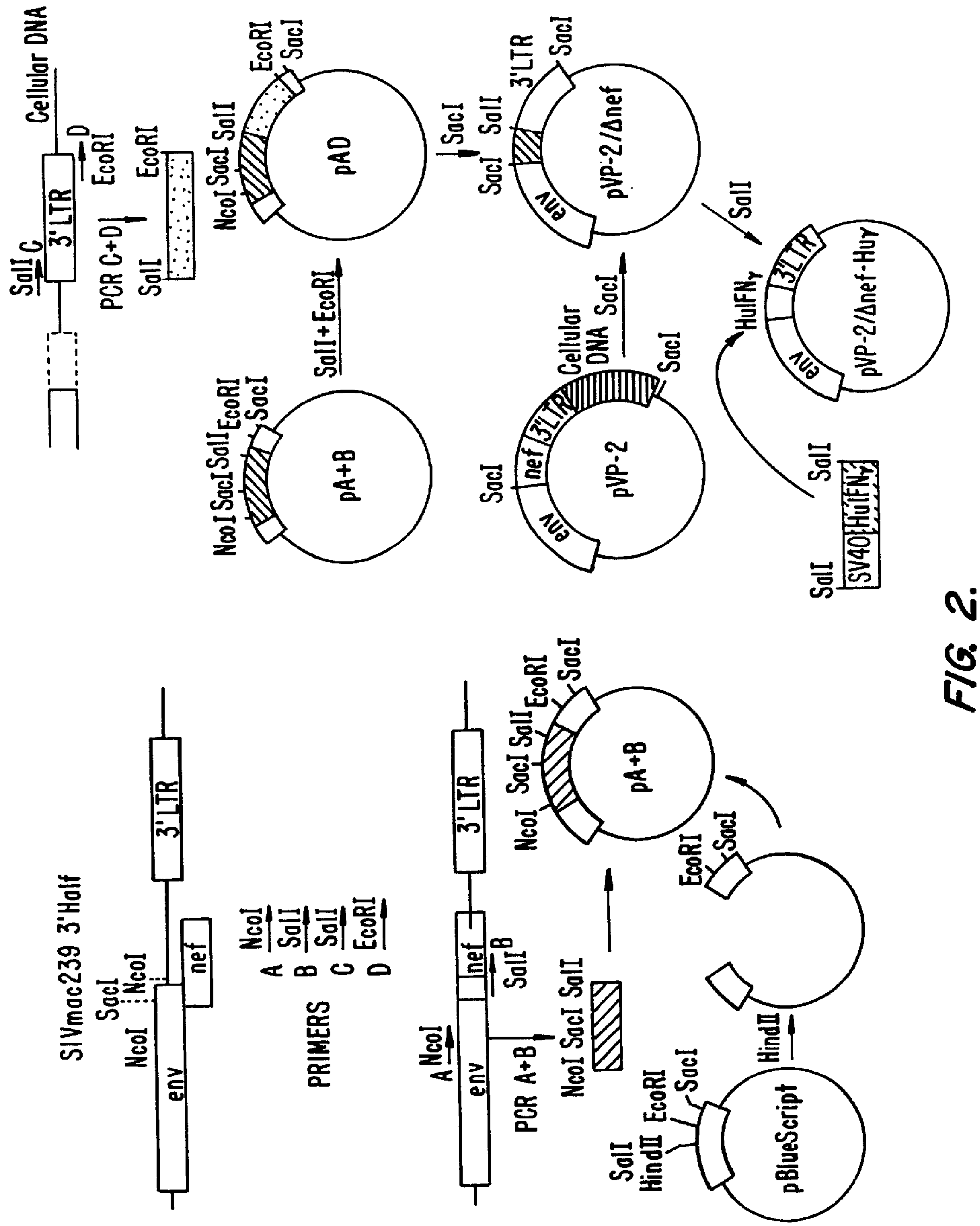
FIG. 2 schematically presents the strategy for making pVP-2/Δnef and pVP-2/Δnef-Huγ.

A fragment extending from the SacI site in the env gene (nt. 9487) to a SacI site in the cellular DNA sequence in pVP-2 was removed by SacI digestion. A similar SacI fragment was isolated from pAD, which contained the same SacI site in env to another SacI site in the polylinker region of pBluescript. The latter SacI fragment was cloned into pVP-2 generate pVP-2/Δnef. The above procedure is schematically represented in FIG. 2 which additionally shows the construction of SIVSV-IFN.

The plasmid pMA239 (kindly provided by Dr. A. Adachi, Kyoto University, Japan) contains the complete $SIV_{mac239}$ proviral genome from a HindIII site in position-41 to an EcoRI site present in the cellular DNA flanking sequences (position 11432) {Shibata, R., et al., *J. Virol.*, 65:3514–3520 (1091)}. Both pMA239 and pVP-2/Δnef plasmids were digested with SphI (nt. 6707) and EcoRI, and the 3' halves were interchanged to produce $pSIV_{239\Delta nef}$. This plasmid contains the $SIV_{mac239}$ provirus with a 186-base deletion in the nef gene and a unique SalI site between the end of env and the beginning of the 3' LTR, and with deletions in most of the 3' end of the cellular DNA flanking sequences. Nucleic acid sequencing was performed to confirm that no changes had been introduced by PCR amplification in SIV sequences.

Construction of SIV vectors expressing IFN-γ.

The plasmid pSV7b (available from Dr. Paul A. Luciw, University of California, Davis, Calif., USA), containing the SV40 early promoter, was modified to eliminate 300 bp of SV40 DNA sequences not involved in transcription regulation. pSV7b was digested with SalI and PvuII, treated with Klenow, and relegated to produce PSVΔ with a SalI site in proximity to gV40 early promoter sequences. The HuIFN-γ gene was obtained as a SmaI cassette from pHuIFN-γ {Giavedoni, L. D., et al., *Proc. Natl. Acad. Sci. USA*, 89:3409–3413 (1992)} and cloned into the SmaI site of pSVΔ. The SV40 early promoter and the HuIFN-γ coding sequences were released as a SalI cassette and inserted in the SalI site of $pSIV_{239\Delta nef}$; because the cloning of this cassette was not directional, both orientations were obtained. Plasmid $pSIV_{239\Delta nef/SV\text{-}\gamma(s)}$ has the SV40 promoter and IFN-γ gene sequences in the same orientation (i.e., sense) as the SIV reading frame, whereas $pSIV_{239\Delta nef/SV\text{-}\gamma(as)}$ has the gene cassette in the opposite orientation (i.e., antisense).

A second set of SIV vectors was engineered to express the IFN-γ gene under the control of SIV regulatory sequences; i.e. utilizing the nef gene splice signals. $pSIV_{239\Delta nef}$ was digested with SalI and its ends were made blunt in a reaction with the Klenow fragment of the DNA polymerase. The HuIFN-γ, obtained as a SmaI cassette from pHuIFN-γ, was cloned into $pSIV_{239\Delta nef}$, and two plasmids with HuIFN-γ in both orientations were obtained. Plasmid $pSIV_{239\Delta nef/\gamma(s)}$ contains the HuIFN-γ gene in the same direction as the SIV genes, whereas $pSIV_{239\Delta nef/\gamma(as)}$ has the HuIFN-γ gene in the opposite orientation.

Finally, a recombinant SIV was generated with mutations in the two ATG codons at the beginning of the nef translation frame. T residues (positions 9334 and 9352) in each ATG codon at the beginning of nef (codon 1 and 10, respectively) were both mutated to C residues to preclude translation initiation. These mutations were made by the site-directed mutagenesis method that utilizes a synthetic mutant oligonucleotide primer. The Muta-Gene Plasmid Kit (Bio-Rad, Richmond, Calif., USA) was used, and details are provided in the manual that accompanies this kit. The DNA fragment from NheI (8998) to SacI (9485) from $SIV_{mac239}$ was subcloned into pTZ18U. DNA template was prepared in a *E. coli* dutung host to allow for incorporation of uracil for thymidine. After in vitro DNA synthesis with the mutant oligonucleotide primer, the wild type strand (i.e., template) containing uracil is selectively eliminated by passage of the synthesis products through a dui$^{+}$ung$^{+}$*E. coli* strain. The mutagenic primer was $^{5'}$CTGACCTACCTA-CAATACGGGTGGAGCTATTTCC ACGAGGCGGT CCAGGCC$^{3'}$, (SEQ ID NO:1) (the two new C residues are underlined and bolded). The mutated SIV clone, pTZ-SIV-MI, was verified by DNA sequencing by the deoxynucleotide chain-termination method. The plasmid pTZ-SIV-MI was digested with NheI (position 8999) and SacI (position 9487), and the 488 bp DNA fragment was purified. Similarly, the $pSIV_{239\Delta nef}$/IFN plasmid was digested with NheI and partially with SacI, and the 12,600 bp DNA fragment was purified. Both DNA fragments were finally ligated to produce $pSIV_{239\Delta nefATG/\gamma}$.

Preparation-of infectious SIV vectors.

Figure 3:
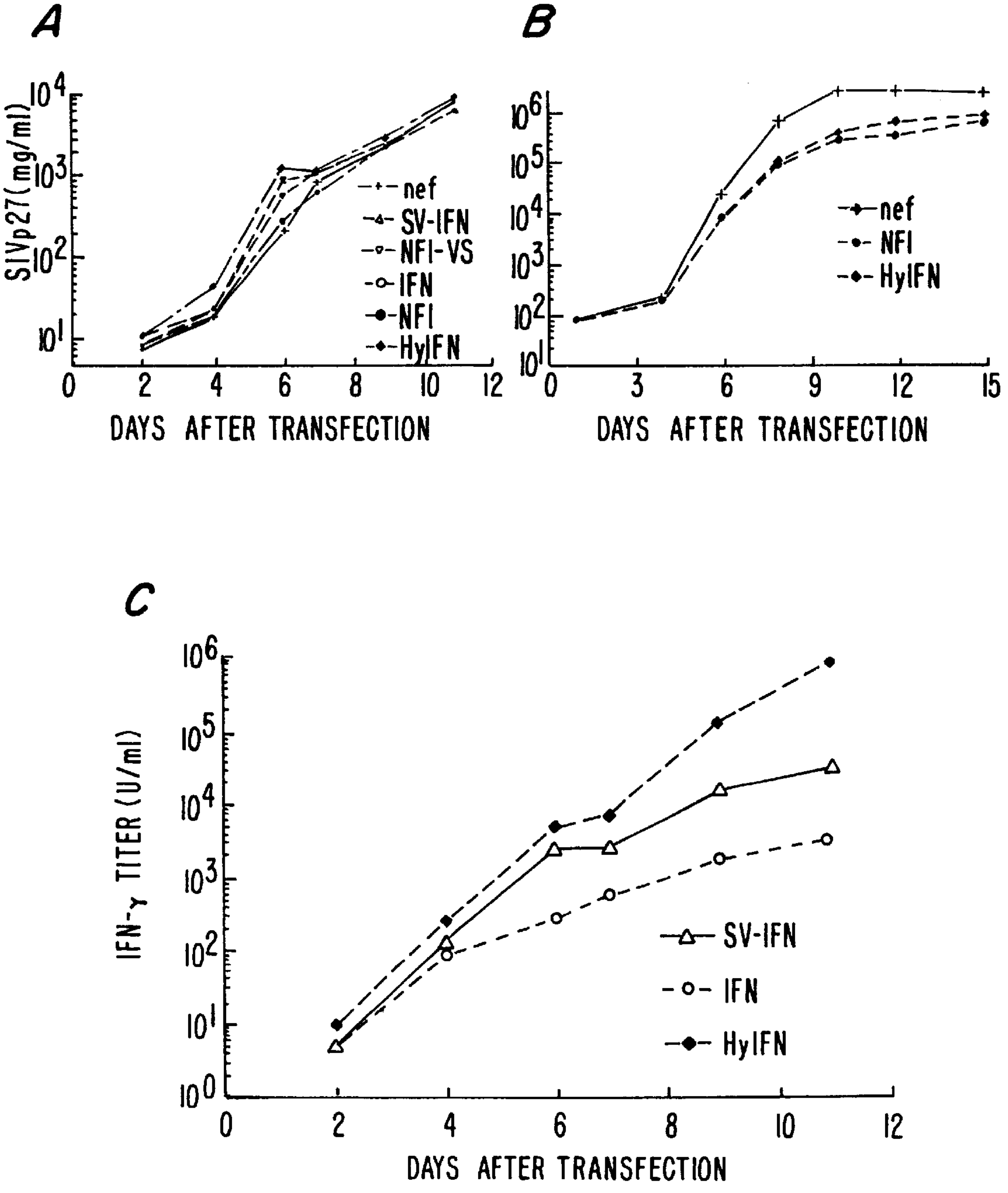
FIGS. 3A to 3C graphically present the data on in vitro replication of SIV vectors. The kinetics of viral replication are shown in FIGS. 3A and 3B. The proviral DNA was employed to generate infectious SIV vectors in A. CEMx174 cells and B. macaque PBMCs.

All plasmids were grown in DH5-α cells. To reduce the instability of plasmid DNA containing retroviral sequences, bacteria containing these plasmids had to be grown at 30° C., with low oxygenation and gentle agitation. Plasmids containing proviral forms of SIV vectors were used to produce infectious viruses by electroporation of CEMx174 cells and macaque PBNCS (FIGS. 3A and 3B, respectively). Briefly, cells in the exponential phase of growth were resuspended in electroporation medium (The electroporation medium consisted of 10mM dextrose, 0.1 mM DTT in RPMI-1640) at a concentration of $1.3\times10^{7}$ cells/ml. A cell suspension of 0.3 ml volume ($4\times10^{6}$ cells) was mixed with 5 μg (100 μl) of plasmid DNA. The DNA-cell mixture was kept on ice for electroporation, and the electroporation conditions were 960 μF and 200 V. After pulsing, cells were removed from the electroporation chamber and resuspended in 5 ml of 10% FCS-RPMI (FCS denotes fetal calf serum). PBMCs were cultured in medium containing 50 U/ml of recombinant human IL-2 (Cetus Corp., Emeryville, Calif., USA). Transfected cells were kept in the exponential growth phase, and the cultures were maintained for no more than 14 days, with daily monitoring to score cytopathic effects. Viral replication was measured by a monoclonal antibody-based, antigen capture enzyme-linked imnmunosorbent assay (ELISA) kit (Coulter Corp, Hialeah, Fla., USA) specific for SIV major core protein p27 (plasma antigenemia) antigen (herein also referred to as "SIV p27") per the kit's instruction. The cutoff for the Coulter SIV ELISA is approximately 75 to 100 pg/ml.

The result is shown in FIGS. 3A and 3B. The solid line with crosses represents $SIV_{\Delta nef}$; broken line with upright triangles represents SIVSV-IFN; broken line with inverted triangles represents SIVNFI-VS; broken line with open circles represents SIVIFN; broken line with solid circles represents SIVNFI; and broken lines with solid diamonds represents SIVHyIFN.

Antiviral activity of INF-γ.

The concentration of human IFN-γ in the supernatant of SIV-infected CEMx174 cultures was determined by measuring its antiviral activity in inhibiting the cytopathic effects (CPE) of EMCV on human A549 cells, according to the standard antiviral assay described in Yilma, T., *Methods Enzymol.*, 119: 551–558 (1985). supernatants from CEMx174 cells infected with SIV vectors were diluted three-fold in DMEM for assay of IFN-γ titers. Aliquots of 50 μl of these dilutions were placed in 96-well plates, and $10^4$ A549 cells in 100 μl of DMEM with 10% FCS were added to each well, After 24 hr of incubation, the cells were challenged with the minimum dose of EMCV ($10^4$ pfu of per well) that gave 100% cpe in cells not treated with IFN-γ. The units of IFN-γ are expressed as the reciprocal of the dilution of sample that gave 50% protection against challenge virus.

The result is shown in FIG. 3C, the solid line with triangles represents IFN-γ production by SIVSV-IFN; broken line with circles represents IFN-γ production by SIV-IFN; and broken line with diamonds represents IFN-γ production by SIVHyIFN.

Stability of SIV vectors.

Figure 4:
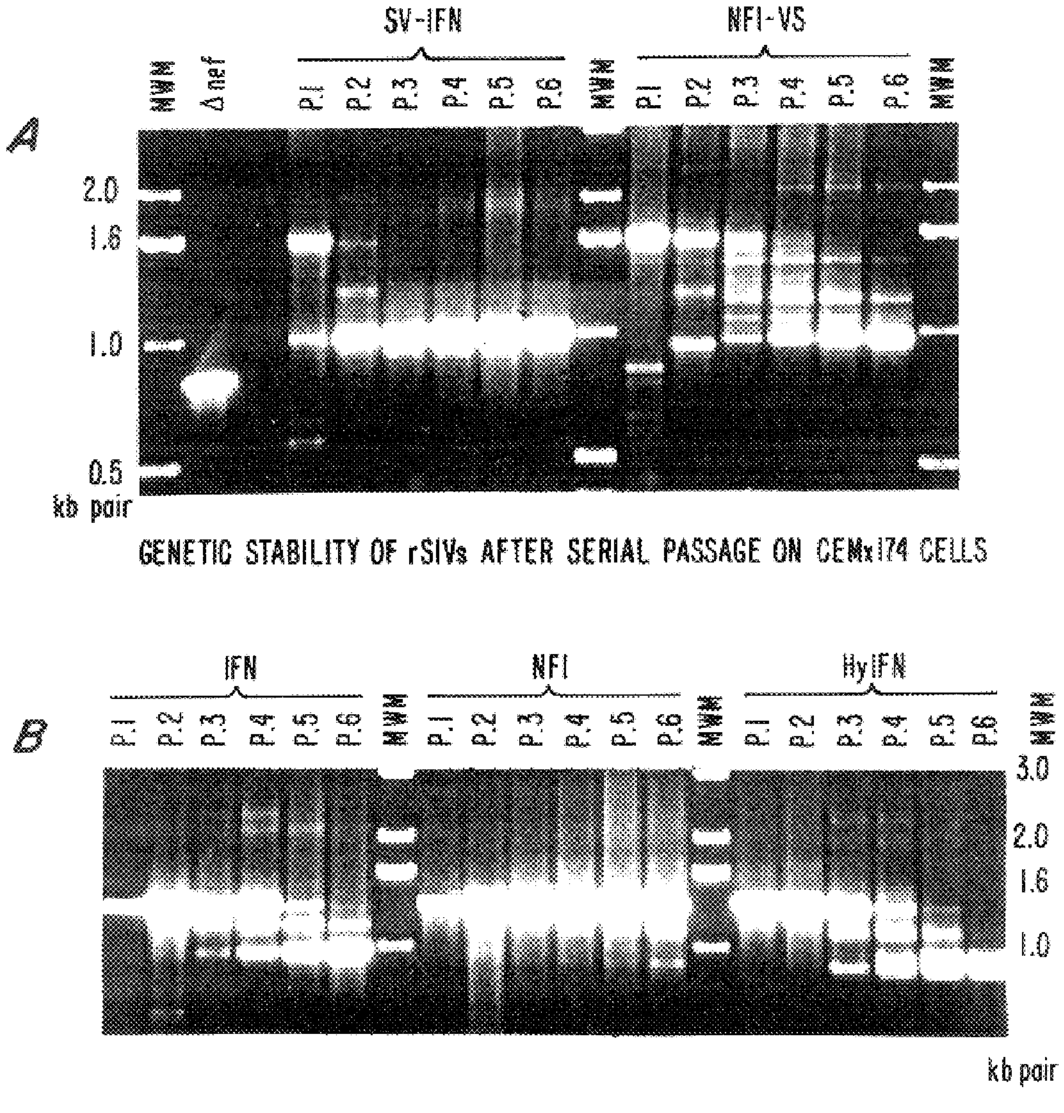
FIGS. 4A and 4B present information regarding the genetic stability of the SIV vectors: SIV239Δnef, SIVSV-IFN, SIVNFI-VS, SIVIFN and SIVNFI, and SIVHyIFN. The notations are as defined in FIG. 1. "P." denotes passage number, e.g., "P. 1" denotes passage number one.

CEMx174 cells were infected with 10 ng of each recombinant virus and maintained in culture for 7 days. Progeny viruses were quantitated by SIVgag-specific ELISA (Coulter Corp., Hialeah, Fla., USA), and 10 ng were then used to infect fresh CEMx174 cells. SIV vectors were passaged in this way seven times. The stability of all SIV vectors were analyzed by PCR amplification of the 3' portion of each viral vector, encompassing the IFN-γ sequences, to determine if deletions occur with serial passage in cell culture (FIGS. 4A and 4B). The primers for PCR amplification were primers A (sense primer, described above) and E ($^{5'}$AAATCCCTTCCAGTCCC CCC$^{3'}$(SEQ ID NO.6), antisense, nt. 9710). PCR reaction conditions were denaturation at 94° C. for 60 seconds, annealing at 65° C. for 60 seconds, and extension at 72° C. for 2 minutes; the number of cycles was 30. FIGS. 4A and 4B present the genetic stability of the $SIV_{\Delta nef}$ vectors. Supernatants from each virus passage were examined for IFN-γ antiviral activity (FIG. 5), the concentration of IFN-γ was determined using the method described for FIG. 3C. The species specificity and the antiviral activity was determined by a human-specific IFN-γ ELISA kit (Intertest-γ, Genzyme Corp, Cambridge, Mass., USA).

RESULTS

Table 1 lists the plasmids and viral vectors that were constructed.

TABLE 2

| Plasmid Fragment[a] | Virus Produced | Remarks | PCR |
|---|---|---|---|
| $pSIV_{239\Delta nef}$ | $SIV_{\Delta nef}$ | nef-deletion virus | 800 bp |
| $pSIV_{239\Delta nef/SV\text{-}\gamma(s)}$ | $SIV_{SV\text{-}IFN}$ | SV40-IFN-γ, sense | 1600 bp |
| $pSIV_{239\Delta nef/SV\text{-}\gamma(as)}$ | $SIV_{NFI\text{-}VS}$ | SV40-IFN-γ, antisense | 1600 bp |
| $pSIV_{239\Delta nef/\gamma(s)}$ | $SIV_{IFN}$ | IFN-γ, sense | 1300 bp |
| $pSIV_{239\Delta nef/\gamma(as)}$ | $SIV_{NFI}$ | IFN-γ, antisense | 1300 bp |
| $pSIV_{239\Delta nefATG/\gamma}$ | $SIV_{HyIFN}$ | nefATGmutation, IFN-γ, sense | 1300 bp |

Replication of SIV vectors expressing IFN-γ.

As shown in FIGS. 3A and 3B, several of the SIV vectors replicated rapidly and reached peak titers by six days after transfection. After 9 days, the amount of SIV p27 in media was similar for all the CEMx174 cultures with SIV vectors. In addition, extensive cytopathology of CEMx174 cells, characterized by multinucleate syncytia, was similar in cultures transfected with all the SIV vectors and $SIV_{mac239}$. However, in PBMCs, $SIV_{\Delta nef}$ replicated faster than SIV vectors.

Expression of lymphokine by SIV vectors.

As shown in FIG. 3C, expression of IFN-γ by SIVHyIFN was rapidly detected by 2 days after transfection, at a time when SIV p27 was barely detectable. Levels of IFN-γ for this recombinant virus were the highest among all vectors tested; after 11 days in culture this vector produced as much as $10^6$ units/ml. In contrast, though cells transfected with SIVSV-IFN expressed readily detectable amounts of IFN-γ, the maximum level (at $3\times10^3$ Units/ml on day 11) was about two orders of magnitude lower than that of SIVHyIFN. Interestingly, of the two SIV vectors with SV40 promoters, only SIVSV-IFN expressed high levels of INF-γ. Cells infected with the vector carrying the antisense orientation (SIVNFI-VS) manifested minimum activity (20 Units/ml) after 11 days in culture. It is postulated that the polyadenylation signals located in the 3'LTR of SIV are important for increasing the stability of IFN-γ mRNAs initiated by the SV40 promoter; these signals are lacking in SIVNFI-VS. In contrast, expression of IFN-γ was significantly lower ($3\times10^3$ unit/ml on day 11), and expression of IFN-γ was undetectable in cultures infected with SIVNFI.

Stability of SIV vectors.

All the SIV vectors containing the IFN-γ gene were unstable and produced deletions after serial passage in CEMX174 cells. The degree of instability appears to depend on the size and the orientation of the insert. SIVSV-IFN and SIVNFI-VS, which contain the 800 bp SV40promoter/IFN-γ insert, deleted part of these heterologous sequences rapidly; for SIVSV-IFN, deletion fragments were detected as early as the first passage (FIG. 4A). SIVSV-IFN and SIVNFI-VS, which contain the 800 bp SV40 promoter/IFN-γ insert, deleted portions of these heterologous sequences rapidly; deletions were detected in SIVSV-IFN as early as the first passage. For SIVIFN and SIVHyIFN, instability was first observed after the third passage; by the sixth passage, PCR amplification analysis failed to detect intact IFN-γ sequences in both of these vectors. In contrast, SIVNFI, which contains the same 500 bp IFN-γ insert but in the opposite orientation, still retained most of the insert after six passages (FIG. 4B).

Figure 5:
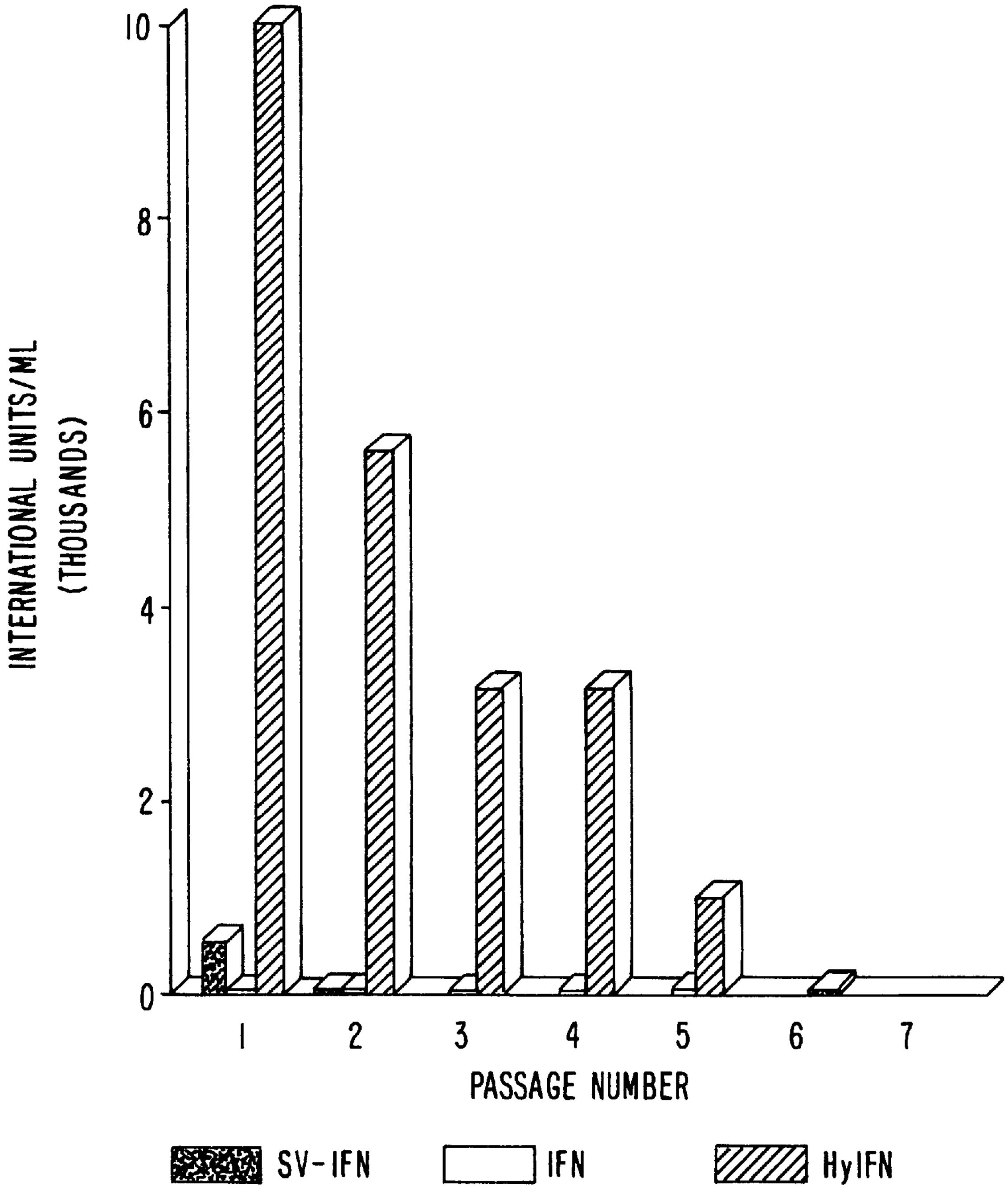
FIG. 5 is a graph presenting the IFN-γ production for each virus passage for vectors SIVSV-IFN, SIVIFN and SIVHy-IFN. The notations are as defined in FIG. 1.

As shown in FIG. 5, expression of IFN-γ by SIVSV-IFN was undetectable by the third passage; this observation is consistent with the rapid deletion of IFN-γ coding sequences from the viral genome. SIVIFN and SIVHyIFN, which are more stable viruses than SIVSV-IFN, continued to produce IFN-γ through the fifth passage. Only SIVHyIFN expressed detectable levels of IFN-γ by the sixth passage, at that point IFN-γ sequences were barely detectable by PCR amplification.

DISCUSSION

Initially, a strong heterologous promoter such as the early SV40 promoter was incorporated into the vectors to achieve a high level of IFN-γ expression. Of the two SIV vectors developed, only SIVSV-IFN expressed high levels of IFN-γ; the vector carrying the antisense orientation, SIVNFI-VS, manifested a minimum activity after several days in culture. It is postulated that the polyadenylation signals located in the 3' LTR of SIV are important for increasing the stability of IFN-γ mRNAs initiated by the SV40 promoter. For SIVNFI-VS, signals for efficient polyadenylation are not available. However, vectors containing SV40 promoter are found to be very unstable, presumably due to the limited capacity of retroviruses to accommodate extra genomic material as well as their tendency to delete sequences not providing a selective advantage for replication.

Due to the high instability of SIVSV-IFN and SIVNFI-VS, a vector was designed to express IFN-γ using the same SIV signals that produce nef mRNA. It was postulated that by reducing the size of the insert (i.e., removing the SV40 early promoter) in the SIV vector, the stability of the vector would be enhanced. Indeed, SIVIFN and SIVNFI are more stable viruses than SIVSV-IFN and SIVNFI-VS. However, confirming the importance of the presence of a strong promoter, the ability of SIVIFN to express IFN-γ is far more limited than that of SIVSV-IFN; for the antisense vector SIVNFI there was no detectable IFN-γ at all. Next, SIV vectors were constructed which expressed IFN-γ under the control of the 5'LTR. However, the nef coding sequences that overlap env were still transcribed by these constructs, reducing the level of IFN-γ translation. To use the SIV transcription machinery in full to increase lymphokine production, the two in-frame nef start codons that were still present in SIVΔnef vector were mutated without altering the env amino acid sequence (FIG. 1). The two nef ATGs were located in the env coding sequence, and they might interfere with the translation of the IFN-γ mRNA. Therefore, the ATGs were mutated without altering the env amino acid sequence. As expected, the new vector SIVHyIFN expressed high amounts of IFN-γ; in a similar fashion as the temporal expression of nef, IFN-γ was detected early after transfection. As it occurred for SIVSV-IFN and SIVNFI-VS, the genetic stability of the vectors carrying the IFN-γ gene with the sense orientation (SIVHyIFN and SIVIFN) was lower than that of SIVNFI. It is postulated that a particular arrangement of certain IFN-γ and 3' LTR sequences is responsible for such instability. Any influence of IFN-γ is ruled out since SIVHyIFN and SIVIFN are equally unstable, and SIVHyIFN expresses more than 100 times IFN-γ than SIVIFN.

Example 2

Recombinant SIV Vector Inoculations of Macaques

This Example describes the inoculation of the recombinant SIV vectors of Example 1 into rhesus macaques to determine their virulence and stability of their IFN-γ inserts. The result shows that SIVHyIFN (SIVmac239Δnef expressing human IFN-γ) is highly attenuated and produces a very low and transient viremia, making it a good candidate for SIV vaccine and also providing the basis for an analogous HIV vaccine, in which the nef gene is deleted from and the human IFN-γ is inserted into the HIV vector.

MATERIALS AND METHODS

Colony-bred, juvenile rhesus macaques seronegative for simian type D retroviruses, simian T-cell leukemia virus, and SIV, housed according to the American Association for Accreditation of Laboratory Animal Care Guidelines, were inoculated with $10^4$ $TCID_{50}$ of SIVΔnef and SIVHyIFN. Six animals received SIVHyIFN, and four received SIVΔnef. Cell-associated virus isolated from lymph node cells (virus isolated according to the method disclosed in Marthas, M. L., et al., *J. Virol.*, 67:6047–6055 (1993), latent or productive, was measured by limiting-dilution assay by co-culturing serial 10-fold dilutions of $10^6$ macaque PBMCs with CEMx174 cells in quadruplicate in a 24-well plate for 4 weeks. Individual wells were assayed for SIV p27 twice weekly. SIV p27 antigen assays were conducted using an ELISA kit as previously described (Lohman. B., et al., *J. Clin. Microbio.*, 29:2187–2192 (1991)), to detect productive virus infection in vivo. Cell-associated virus levels were calculated according to the method of Reed/Muench method {Reed, L., et al., *Am. J. Hyg.*, 27:493–497 (1938)} and expressed as $TCID_{50}$ per $10^6$ PBMC. Values<1 represent negative cultures for all wells containing $10^6$ PBMCs.

RESULTS

Only PBMCs of SIVΔnef-inoculated macaques had detectable virus in the first week's samples: titers remained generally high through week 12, although there was individual variation. In contrast, SIVHyIFN-vaccinated macaques had low virus titers that were undetectable until week two (Table 3).

SIV p27 was undetectable in SIVHyIFN-inoculated animals, whereas 3 out of 4 animals in the SIVΔnef group (#26740, #26890 and #27149) were slightly positive for SIV p27 on week two.

TABLE 3

Cell-associated virus load in PBMCs of vaccinated thesus macaques

| | | Time after Inoculation | | | | | |
|---|---|---|---|---|---|---|---|
| Macaque # | Virus | 1 Week | 2 Weeks | 4 Weeks | 6 Weeks | 8 Week | 12 Week |
| 26595 | $SIV_{HyIFN}$ | <1 | 47 | 16 | 3 | 1 | 3 |
| 26704 | $SIV_{HyIFN}$ | <1 | 214 | 7 | 3 | 1 | 1 |
| 26919 | $SIV_{HyIFN}$ | <1 | 316 | 32 | 32 | 1 | 1 |
| 27047 | $SIV_{HyIFN}$ | <1 | 3 | 32 | 2 | 10 | <1 |
| 27078 | $SIV_{HyIFN}$ | <1 | <1* | <1 | <1 | <1 | <1 |
| 27178 | $SIV_{HyIFN}$ | <1 | 1 | 3 | 148 | 2 | 10 |
| 26720 | $SIV_{\Delta nef}$ | 68 | 676 | 10 | 10000 | 25 | 3 |
| 26740 | $SIV_{\Delta nef}$ | 5 | 1795 | 316 | 2371 | 21 | 1 |
| 26890 | $SIV_{\Delta nef}$ | 468 | 316 | 2138 | 100 | 10000 | 4677 |
| 27149 | $SIV_{\Delta nef}$ | 47 | 1000 | 100 | 3162 | 31622 | >100000 |

*Virus was isolated from lymph node cells.

Because of its bearing on vaccine safety and efficacy, the in vivo stability of STVHyIFN was also studied. By week two, the virus isolated from only 1 of the 6 SIVHyIFN-vaccinated animals (#26704) had deleted the IFN-γ insert, and the culture supernatant had no detectable antiviral activity. In week four, virus from 3 animals (#26595, #26919, #27047) still retained the insert and antiviral activity was present. By week 6, only virus isolated from lymphocytes of macaque #27047 retained the IFN-γ gene and had antiviral activity in culture. By week 12, no viruses with full-length IFN-γ genes could be isolated, and no antiviral activity was detected in cultures infected with these viruses. Remarkably, this deletion did not lead to an increase in virus load. The progressive deletion of the IFN-γ gene in vivo appears to have a positive cumulative effect in generating a vigorous, stepwise protective immune response. Initially the immune system is alerted by exposure to a highly attenuated virus along with IFN-γ. As virulence increases to the level of SIVΔnef through loss of the IFN-γ gene, the emerging virus is met by an immune system primed for the encounter by the earlier exposure to SIVHyIFN. Finally, a challenge by a fully pathogenic strain may therefore be resisted.

In summary, only SIVΔnef has provided significant protection against challenge with pathogenic $SIV_{mac251}$. However, persistence of SIVΔnef and the limited protection it provides for the first year after immunization restrict its use as a vaccine. The present invention presents the construction and characterization of SIVHyIFN ($SIV_{mac239\Delta nef}$ expressing IFN-γ), that is highly attenuated and produces a very low and transient viremia. This approach, involving the incorporation of IFN-γ or other lymphokines, are useful for the development of a safe and efficacious vaccine for HIV, and diseases caused by HIV such as AIDS and ARC.

Example 3

At 25 weeks post-immunization the six macaques inoculated with SIVHyIFN, the four inoculated with SIVΔnef, plus two naive controls, were challenged with 100 $AID_{50}$ (animal infectious dose 50) of $SIV_{mac251}$. The viral inoculum was given intravenously, in a single, 1 ml dose. $SIV_{mac251}$ is a pathogenic biological isolate that has been grown in rhesus monkey peripheral blood mononuclear cells, and has been titered in rhesus monkeys {Lewis, et al., *AIDS Research and Human Retroviruses*, 10:213–220 (1994)}.

Viral loads for the 12 animals were determined as in Example 2, at different time points, and are shown in Table 4, below. Although the challenge virus could be isolated from all 12 macaques, the mean viral load for the SIVHyIFN-vaccinated animals was lower than the one for the SIVΔnef group in the first 6 weeks after challenge. At more than 18 weeks into the post-challenge period, both unimmunized controls had to be euthanized due to severe AIDS-related complications.

This challenge experiment demonstrates that SIVHyIFN is an attenuated virus that replicates at lower levels than SIVΔnef, but induces similar or better levels of immunity against a challenge with a pathogenic SIV.

TABLE 4

Virus Loads after challenge ($TCID_{50}$ per million PBMC)

| Macaques vaccinated w/**$SIV_{HyIFN}$** | 0 WPC | 1 WPC | 2 WPC | 4 WPC | 6 WPC | 8 WPC | 12 WPC | |
|---|---|---|---|---|---|---|---|---|
| 26595 | <1 | <1 | 10 | <1 | 32 | 100 | 215 | |
| 26704 | 316 | <1 | 32 | 3 | 100 | 32 | 215 | |
| 26919 | <1 | 47 | 1000 | 1479 | 1000 | 3162 | 171 | |
| 27047 | 10 | 21 | <1 | 316 | 32 | 100 | 1000 | |
| 27078 | <1 | <1 | <1 | 3 | 3 | 3 | 46 | |
| 27178 | 18 | 3 | 316 | 316 | 32 | 1000 | 3162 | |
| **Macaques vaccinated with $SIV_{\Delta nef}$** | **0 WPC** | **1 WPC** | **2 WPC** | **4 WPC** | **6 WPC** | **8 WPC** | **12 WPC** | |
| 26720 | 1 | <1 | 32 | 100 | 215 | 215 | 32 | |
| 26740 | 10 | 32 | 32 | 2153 | 3162 | 316 | 316 | |
| 26890 | 316 | 171 | 31622 | 1000 | 1000 | 31622 | 3162 | |
| 27149 | 316 | 1795 | 3162 | 316 | 316 | 2153 | 4645 | |
| **NAIVE Macaques** | **0 WPC** | **1 WPC** | **2 WPC** | **4 WPC** | **6 WPC** | **8 WPC** | **12 WPC** | |
| 26658 | <1 | 215 | 2153 | 316 | 316 | 3162 | N.D. | Died on week 18 |
| 26905 | <1 | 316 | 14791 | 3162 | 3162 | 3162 | 464 | Died on week 12 |

Bold font: mixed infection (vaccine and challenge virus)
"WPC" denotes the number of weeks post challenge.

Example 4

Recombinant HIV Vector constructions and Characterizations

This Example describes the construction and characterization of a replication-competent HIV vectors expressing IFN-γ.

MATERIALS AND METHODS

Cells and Viruses.

CEMx174 and Hut78 cells, and human PBMCs are used for HIV isolation and propagation; these cells are maintained in RPMI (Roswell Park Memorial Institute Medium) supplemented with 10% fetal bovine serum. Human A549 cells (American Type Culture Collection, Rockville, Md., USA) are propagated in Dulbecco's modified Eagle's (DMEM) supplemented with 10% fetal bovine serum and antibiotics. HIVMN and derivatives of the virus are propagated in human PBMC. Encephalomyocarditis virus (EMCV) for the antiviral assay of human IFN-γ (HuIFN-γ) is propagated in A549 cells.

Construction of HIVMNΔnef.

The molecular clone HIVMN is used to construct HIV vectors {Gurgo, C., et al., *Virology*, 164:531–536 (1988). GenBank Accession Number M17449}. Two sets of mutations are made in order to introduce two NcoI sites at positions 8816 and 9281 of the HIVMN genome. These mutations are made by the site-directed mutagenesis method that utilizes a synthetic mutant oligonucleotide primer. The Muta-Gene Plasmid Kit (Bio-Rad, Richmond, Calif., USA) is used, and details are provided in the manual that accompanies this kit. The DNA template is prepared in a *E. coli* dut-ung- host to allow for incorporation of uracil for thymidine. After in vitro DNA synthesis with the mutant oligonucleotide primer, the wild type strand (i.e., template) containing uracil is selectively eliminated by passage of the synthesis products through a dut+ung+*E. coli* strain.

The mutagenic primers are (mutated nucleotides appear in capitals):

32 mer: (nt. 8803) 5'gctataagTtgggCggcCGCtggt-caaaaacg3' (SEQ ID NO:7) sense orientation;

26 mer: (nt. 9271) 5'ctctcctttaGCggccGcttctatct3' (SEQ ID NO.8) antisense orientation.

The 32 mer is used in the first mutagenic reaction to introduce a NotI site between the coding regions for env and nef. After changes have been confirmed by DNA sequencing, the 26 mer oligonucleotide is employed to create a second NotI restriction site, which is located in the 3'LTR. Finally, a digestion with the NotI endonuclease releases a 464 bp fragment that contains most of the nef sequence. The final product is pHIVMNΔnef, a plasmid that contains a HIVMN proviral DNA lacking the net gene and containing a unique NotI cloning site at position 8816.

Construction of HIV vectors expressing IFN-γ.

The HuIFN-γ gene is obtained as a SmaI cassette from pHuIFN-γ {Giavedoni, L. D., et al., *Proc. Natl. Acad. Sci. USA*, 89:3409–3413 (1992)}. NotI linkers (5'agcggccgct3', non-phosphorylated, Promega Corporation, Madison, Wis., USA) are added to this HuIFN-γ fragment using T4 DNA ligase, and then the DNA is digested with NotI. pHIVMNΔnef is also digested with NotI and both fragments are linked together. Because the cloning of this cassette is not directional, both orientations are obtained. Plasmid pHIVMNΔnef has IFN-γ gene sequence in the same orientation (i.e., sense) as the HIV reading frame, whereas pHIVMN-NFI has the gene cassette in the opposite orientation (i.e., antisense).

Preparation of infectious HIV vectors.

All plasmids are grown in DH5-α cell. To reduce the instability of plasmid DNA containing retroviral sequences, bacteria containing these plasmids had to be grown at 30° C., with low oxygenation and gentle agitation. Plasmids containing proviral forms of HIV vectors are used to produce infectious viruses by electroporation of human PBMCs. Briefly, cells in the exponential phase of growth are resuspended in electroporation medium. (The electroporation medium consisted of 10 mM dextrose, 0.1 mM DTT in RPMI-1640) at a concentration of $1.3\times10^7$ cells/ml. A cell suspension of 0.3 ml volume ($4\times10^6$ cells) is mixed with 5 μg (100 μl) of plasmid DNA. The DNA-cell mixture is kept on ice for electroporation, and the electroporation conditions are 960 μF and 200 V. After pulsing, cells are removed from the electroporation chamber and resuspended in 5 ml of 10% FCS-RPMI (FCS denotes fetal calf serum). PBMCs are cultured in medium containing 50 U/ml of recombinant human IL-2 (Cetus Corp., Emeryville, Calif., USA). Transfected cells are kept in the exponential growth phase, and the cultures are maintained for no more than 14 days, with daily monitoring to score cytopathic effects. Viral replication is measured by a monoclonal antibody-based, antigen capture enzyme-linked immunosorbent assay (ELISA) kit (Coulter Corp, Hialeah, Fla., USA) specific for HIV major core protein p27 (plasma antigenemia) antigen (herein also referred to as "HIV p27") per the kit's instruction. The cutoff for the Coulter HIV ELISA is approximately 75 to 100 pg/ml.

Antiviral activity of IFN-γ.

The concentration of human IFN-γ in the supernatant of HIV-infected PBMCs cultures is determined by measuring its antiviral activity in inhibiting the cytopathic effects (CPE) of EMCV on human A549 cells, according to the standard antiviral assay described in Yilma, T., *Methods. Enzymol*, 119:551–558 (1985). Supernatants from PBMC infected with HIV vectors are diluted three-fold in DMEM for assay of IFN-γ titers. Aliquots of 50 μl of these dilutions are placed in 96-well plates, and 104 A549 cells in 100 μl of DMEM with 10% FCS are added to each well. After 24 hr of incubation, the cells are challenged with the minimum dose of EMCV ($10^4$ pfu of per well) that gave 100% cpe in cells not treated with IFN-γ. The units of IFN-γ are expressed as the reciprocal of the dilution of sample that gave 50% protection against challenge virus. These vectors that express IFN-γ are tested in Example 5, below.

Example 5

Testing of the Recombinant HIV Vector

The attenuated live recombinant HIV of Example 4 is first tested in chimpanzees for their ability to elicit protection against, or significantly delay infection of, HIV-1 by immunization.

MATERIALS AND METHODS

Adult male chimpanzees (*Pan troglodytes*) that have been used previously in hepatitis A, B, and non-A non-B experiments will be maintained at the Laboratory for Experimental Medicine and Surgery in Primates, in biosafety level 3 facilities. All experimental procedures are done according to institutional guidelines for containment of infectious diseases and for humane care of primates {Moor-Jankowski, J., et al. , *J. Med. Primatol*., 18:1–26 (1989)}.

Immunogens.

*The live attenuated recombinant HIV of Example* 4 above.

Challenge Virus.

The challenge inoculum, in phosphate buffered saline solution, is from a stock of HIV-1, either strain HIV-1 SF2 or HTLV-IIIB (available from the National Institute of Health, NIH, Bethesda, Md., USA), which have been titrated in chimpanzees and used in other HIV vaccine challenge studies {Arthur, L. O., et al., *J. Virol*., 63:5046–5053 (1989) Berman, P. W., et al., *Nature* (London), 345:622–625 (1990) }. The infectivity titer of this HIV-1 stock is considered to be $10^4TCID_{50}$ per ml and $4\times10^3$ infectious units per ml for chimpanzees. The chimpanzees are challenged i.v. with 1 ml of a 1:100 dilution. Aliquots of these same 1:100 dilutions are titrated in quadruplicate by 2-fold serial dilution and infection of H9 cells in 96-well microtiter plates. After 6 days, infections is scored by immunofluorescence assay.

Neutralization Assay.

Neutralization activity in serum samples from immunized chimpanzees is determined by inhibition of syncytia formation in CEM-SS cells, as described {Nara, P. L. , et al., *AIDS Res. Hum. Retroviruses*, 3:283–302 (1987)}, or inhibition of immunofluorescent foci in H9 cells.

Virus Isolation.

PBMC or bone marrow cells (obtained as aspirates) from challenged chimpanzees are cultured with normal human PBMC {Fultz, P. N., et al., *J Virol*., 58:116–124 (1986)}. $CD4^+$-enriched lymphocytes are obtained from chimpanzee PBMC by separation with magnetic beads to which are attached monoclonal antibodies specific for the CD8 antigen (Dynabeads, Robbins Scientific, Mountain View, Calif., USA). Lymph node tissue obtained by biopsy is minced with scissors and cultured with human PBMC. All cultures are maintained and monitored for reverse transcriptase activity for 6 weeks before being discarded.

Polymerase Chain Reaction (PCR).

Both single- and double-round (nested) PCR are performed. Single-round PCR is as described {Laure, F., et al., *Lancet*, ii:538–541 (1988)}. The positive control consists of DNA from the 8E5 cell line persistently infected with lymphadenopathy-associated virus type 1 (LAV-1). For nested PCR, and in the case of HTLV-IIIB, the primers for the first round of PCR {Mullis, K. B., et al., *Methods Enzymol.*, 155:335–350 (1987)} are:

5'-GCTTCTAGATAATACAGTAGCAACCCTCTATTG-3' (SEQ ID NO.9), corresponding to a 3-base clamp sequence, an XbaI restriction site, and nucleotides 1025–1048 of the pHXB2 genome {Myers, G., et al., *Human Retroviruses and AIDS*, Los Alamos Nat'l. Lab., Los Alamos, N. Mex., USA (1990)}; and 5'-GTCGGCCTTAAAGGCCCTGGGGCTTGTTCCATC TATC-3' (SEQ ID NO.10), corresponding to a 3-base clamp sequence, a NotI restriction site, and nucleotides 5573–5553 of the pHXB2 genome {Myers, G., et al., *Human Retroviruses and AIDS*, Los Alamos Nat'l. Lab., Los Alamos, N. Mex., USA (1990)}. From the first round, 2.5 μl of the product is reamplified with primers SK145 and SK150 {Kwok, S., et al., *PCR Protocols. A Guide to Method and Applications*, eds. Innis, M. A., et al. (Academic, San Diego), pp. 337–347 (1990)} over a region from nucleotides 1366 to 1507 on the pHXB2 genome.

Challenge with Infectious HIV.

Chimpanzees with sustained neutralizing antibody titers are challenged with infectious HIV 6 months after vaccination with the recombinant live attenuated HIV. The chimpanzees are challenged by i.v. inoculation of 100 $TCID_{50}$ (40 chimpanzee infectious doses) of HIV-1. The challenge is done the game time as that of a naive control animal. Virus is isolated from the PBMC of the naive chimpanzees at 2 weeks postinoculation as well as at all subsequent times to show the HIV-1 stock readily infect the chimpanzees under the conditions of the present experiment.

Attempts to Isolate HIV from Immunized and Challenged Chimpanzees.

Three methods are used to assess the infection status of the animals. (i) Attempts to detect HIV sequences in lymphoid cells by PCR are made periodically {Laure, F., et al., *Lance*, ii:538–541 (1988); Mullis, K. B., et al., *Methods Enzymol.*, 155:335–350 (1987); Kwok, S., et al., in *PCR Protocols: A Guide to Method and Applications*, eds. Innis, M. A., et al. (Academic, San Diego), pp. 337–347 (1990)}. DNA samples obtained from PBMC of the three chimpanzees at 3 weeks and 3 and 6 mo. after challenge are tested. At 6 months after challenge, nested sets of primers are used to perform PCR analyses on both PBMC and lymph node tissue of the challenged and control chimpanzees {Mullis, K. B., et al., *Methods Enymol.*, 155:335–350 (1987)}. This technique is more sensitive than standard PCR, and these experiments are repeated at least seven times on all samples.

(ii) At weeks 2, 4, 6, and 8, and at monthly intervals thereafter, attempts are made to isolate virus from PBMC by cocultivation of the chimpanzees' PBMC with lymphocytes obtained from normal humans. {Fultz, P. N., et al., *J. Virol.*, 58:116–124 (1986)}. Because $CD8^+$ cells have been shown to suppress virus replication not only in HIV-infected humans {Walker, C. M., et al., *Science*, 234:1563–1566 (1986); Tsubotaf H., et al., *J. Exp. Med.*, 169:1421–1434 (1989)} and chimpanzees but also in simian immunodeficiency virus-infected macaques {Tsubota, H., et al., *J. Exp. Med.*, 169:1421–1434 (1989)}, in some experiments chimpanzee PBMC may be depleted of $CD8^+$ lymphocytes before cultures were established. Thus, assays are conducted to detect the virus from either total PBMC or $CD4^+$-enriched cells from the vaccinated chimpanzees during the follow-ups.

At 6 mo. postinoculation, inguinal lymph node biopsies are performed on all animals as well as on uninfected and HIV-infected control chimpanzees. Assays to detect the virus are conducted upon cocultivation with normal human PBMC, the lymph node of the infected control, and the immunized and challenged chimpanzees. The assays are also conducted on bone marrow obtained 37 weeks after challenge.

(iii) Immunoblot analysis (Diagnostic Pasteur, Marnes la Coquette, France) are conducted to determine the humoral immune response of the chimpanzees; and to detect any increases in apparent levels in antibodies to any HIV-specific proteins. Also, using purified antigens in immunoblot assays, antibodies to the nef proteins are assayed for in serum from vaccinated chimpanzee, during 12-mo. follow-up.

The live attenuated virus that remains at very low virus loads, and which preferably maintains the protective immune response of the chimpanzee to challenge with pathogenic HIV according to the battery of tests described above will be the preferred vaccine of the present invention. The most preferred live attenuated virus is one which does not persist in the chimpanzee.

All publications and patent applications mentioned in this Specification are herein incorporated by reference to the same extent as if each of them had been individually indicated to be incorporated by reference.

Although the foregoing invention has been described is in some detail by way of illustration and example for purposes of clarity and understanding, it will be obvious that various modifications and changes which are within the skill of those skilled in the art are considered to fall within the scope of the appended claims. Future technological advancements which allows for obvious changes in the basic invention herein are also within the claims.

We claim:

1. A vector, comprising: a nucleic acid molecule from a lentivirus, the nucleic acid molecule comprising:

(a) a lentiviral 5'-LTR sequence;

(b) a sequence encoding a cytokine;

(c) a sequence encoding a lentiviral env protein, wherein:

(i) the sequence encoding the lentiviral env protein comprises a sequence from a lentiviral nef gene;

(ii) at least one nef start codon is modified or deleted; and (iii) the sequence encoding the lentiviral env protein is upstream of the sequence encoding the cytokine such that expression of the cytokine is enhanced compared to expression of the cytokine from a vector in which the nef start codons in the sequence encoding the lentiviral env protein have not been modified or deleted; and (d) a lentiviral 3'-LTR sequence.

2. The vector of claim 1, wherein said vector encodes an attenuated lentivirus said attenuated lentivirus expresses about $10^6$ Units of said cytokine per milliliter of cell culture about 11 days after transfection with said attenuated lentivirus in vitro.

3. The vector of claim 1, wherein said vector does not express nef.

4. The vector of claim 1, wherein said modified lentiviral nef start codon comprises an ACG sequence.

5. The vector of claim 1, said vector further comprising one or more nucleic acid molecules that encode a lentiviral protein selected from the group consisting of: tat, vis, vpr, and vpf.

6. The vector of claim 1, wherein said sequence encoding the lentiviral envelope protein comprises two modified lentiviral nef start codons.

7. The vector of claim 6, wherein each modified lentiviral nef start codon comprises an ACG sequence.

8. The vector of claim 1, wherein said cytokine is interferon-α, interferon-β, or interferon-γ.

9. The vector of claim 1, wherein said cytokine is a lymphokine selected from the group consisting of: interleukin-2, and interleukin-12.

10. The vector of claim 1, wherein said lentivirus is HIV or SIV.

11. A vector, comprising: a nucleic acid molecule, said nucleic acid molecule comprising:

(a) a lentiviral 5'LTR;

(b) a first nucleotide sequence that encodes a lentiviral gag protein;

(c) a second nucleotide sequence that encodes a lentiviral pol protein;

(d) a third nucleotide sequence that encodes a lentiviral env protein, wherein the third nucleotide sequence comprises a sequence from a lentiviral nef gene and at least one nef start codon is modified or deleted, wherein said modified start codon is a sequence other than ATG, and the deleted or modified lentiviral nef start codon enhances expression of the sequence encoding the cytokine compared to the expression of a cytokine from a nucleic acid comprising an unmodified start codon;

(e) a fourth nucleotide sequence encoding a cytokine, wherein the fourth nucleotide sequence is downstream from the third sequence; and (f) a lentiviral 3'-LTR.

12. The vector of claim 11, wherein said vector encodes an attenuated lentivirus said attenuated lentivirus expresses about $10^6$ Units of said cytokine per milliliter of cell culture about 11 days after transfection with said attenuated lentivirus in vitro.

13. The vector of claim 12, wherein said lentivirus is HIV or SIV.

14. The vector of claim 11, wherein the vector does not express nef.

15. The vector of claim 11, wherein said at least one more lentiviral nef start codon does not alter the amino acid sequence of said env protein.

16. The vector of claim 11, wherein said modified lentiviral nef start codon comprises an ACG sequence.

17. The vector of claim 11, said vector further comprising one or more nucleic acid molecules that encode a lentiviral protein selected from the group consisting of tat, vif, vpr, and vpf.

18. The vector of claim 11, wherein said third nucleotide sequence comprises two modified lentiviral nef start codons.

19. The vector of claim 18, wherein each modified codon comprises an ACG sequence.

20. The vector of claim 11, wherein said cytokine is interferon-α, interferon-β, or interferon-γ.

21. The vector of claim 11, wherein said cytokine is a lymphokine selected from the group consisting of: interleukin-2, and interleukin-12.

* * * * *

UNITED STATES PATENT AND TRADEMARK OFFICE

CERTIFICATE OF CORRECTION

PATENT NO. : 6,326,007 B1 
DATED :December 4, 2001
INVENTOR(S) : Yilma et al.

It is certified that error appears in the above-identified patent and that said Letters Patent is hereby corrected as shown below:

Column 29,
Line 54, please delete the word "vis" and insert therefor -- vif --
Line 57, please delete the word "envelope" and insert therefor -- env --

Signed and Sealed this

Third Day of September, 2002

Attest:

JAMES E. ROGAN

*Attesting Officer* *Director of the United States Patent and Trademark Office*